US007985541B2

(12) United States Patent
Huang et al.

(10) Patent No.: US 7,985,541 B2
(45) Date of Patent: Jul. 26, 2011

(54) QUANTITATIVE ASSAY FOR DETECTION OF NEWLY SYNTHESIZED RNA IN A CELL-FREE SYSTEM AND IDENTIFICATION OF RNA SYNTHESIS INHIBITORS

(75) Inventors: Mingjun Huang, Potomac, MD (US); Yongnian Sun, Hamden, CT (US); Wengang Yang, Madison, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 687 days.

(21) Appl. No.: 10/593,683

(22) PCT Filed: Mar. 23, 2005

(86) PCT No.: PCT/US2005/009959

§ 371 (c)(1), (2), (4) Date: Sep. 20, 2006

(87) PCT Pub. No.: WO2005/095655

PCT Pub. Date: Oct. 13, 2005

(65) Prior Publication Data

US 2007/0141558 A1 Jun. 21, 2007

Related U.S. Application Data

(60) Provisional application No. 60/555,765, filed on Mar. 24, 2004.

(51) Int. Cl.
*C12Q 1/68* (2006.01)
*C07H 21/02* (2006.01)

(52) U.S. Cl. ......................... 435/6; 435/91.51; 536/23.1

(58) Field of Classification Search ........................ None
See application file for complete search history.

(56) References Cited

U.S. PATENT DOCUMENTS

| | | | | |
|---|---|---|---|---|
| 3,642,771 | A * | 2/1972 | Gauri | 536/28.54 |
| 5,614,403 | A * | 3/1997 | Ramig et al. | 435/235.1 |
| 6,004,754 | A * | 12/1999 | You | 435/6 |
| 6,447,994 | B1 | 9/2002 | Schmidt et al. | |
| 6,630,343 | B1 * | 10/2003 | Bartenschlager | 435/320.1 |
| 2002/0164722 | A1 * | 11/2002 | De Francesco et al. | 435/91.2 |
| 2003/0004122 | A1 * | 1/2003 | Beigelman et al. | 514/44 |
| 2003/0054382 | A1 * | 3/2003 | Favre | 435/6 |

FOREIGN PATENT DOCUMENTS

| | | |
|---|---|---|
| DE | 19915178 A1 * | 10/2000 |
| WO | WO 97 47640 | 6/1997 |
| WO | WO 00 33635 | 12/1999 |
| WO | WO 00 40759 | 1/2000 |

OTHER PUBLICATIONS

Hess et al. Phosphorylation assays for proteins of the two-component regulatory system controlling chemotaxis in *Escherichia coli*. Methods in Enzymology 200:188-204 (1991).*

Bartenschlager Sequence Alignment (Sep. 2008; 13 pages).*

Gifford et al. Multiprobe RNase protection assay analysis of mRNA levels for the *Escherichia coli* oxidative DNA glycosylase genes under conditions of oxidative stress. J. Bacteriol. 182(19):5416-5424, Oct. 2000.*

Mueller et al. Transcriptional regulation of the mitochondrial genome of yeast *Saccharomyces cerevisiae*. Journal of Biological Chemistry 261(25):11756-11764, Sep. 1986.*

Biosis, Biosciences Information Service, Philidelphia, PA. Prabu, R. et al. "Development of Small Interfering RNA (siRNAs) Against Full-Length Hepatitis C Virus La Strain," Database Aceension No. PREV20040016583, Abstract, Heptology 38(4) Supp. 1: 220A. 54 Annual Meeting of the American Association for the Study of Lives Diseases., Boston, MA USA. Oct. 24-28, 2003.

Hardy, R.W. et al. "Hepatitis C Virus RNA Synthesis in a Cell-Free System Isolated from Replicon-Containing Hepatoma Cells," Journal of Virology (2003) 77(3): 2029-2037.

Lai, V.H.C. "In Vitro RNA Replication Directed by Replicase Complexes Isolated from the Subgenomic Replicon Cells of Hepatitis C Virus," Journal of Virology (2003) 77(3): 2295-2300.

Zhong, Weidong. "Dinucleotide Analogues as Novel Inhibitors of RNA-Dependent RNA Polymerase of Hepatitis C Virus," Antimicrobial Agents and Chemotherapy (2003) 47(8): 2674-2681.

International Search Report for International Application No. PCT/US2005/009959. Dated Mar. 23, 2005.

Written Opinion of the International Searching Authority for International Application No. PCT/US2005/009959. Dated Mar. 23, 2005.

* cited by examiner

*Primary Examiner* — Samuel C Woolwine
(74) *Attorney, Agent, or Firm* — Cantor Colburn LLP

(57) ABSTRACT

Methods for detecting populations of newly synthesized and newly initiated RNAs in a cell-free system are described. Suitable templates for the populations of newly synthesized and newly initiated RNAs are viral replicon RNAs, particularly HCV viral replicon RNA. The newly synthesized and newly initiated RNAs may be formed in the presence of a labeled nucleotide analog suitable for detection and/or quantitation of the RNAs. The assay may be employed to identify small molecule inhibitors of RNA synthesis of positive strand RNA viruses such as Hepatitis C Virus.

6 Claims, 2 Drawing Sheets

SEQUENCE LISTING

```
<160> NUMBER OF SEQ ID NOS: 8

<210> SEQ ID NO 1
<211> LENGTH: 7989
<212> TYPE: DNA
<213> ORGANISM: Hepatitis C virus

<400> SEQUENCE: 1
```

-continued

```
gccagccccc gattgggggc gacactccac catagatcac tcccctgtga ggaactactg     60
tcttcacgca gaaagcgtct agccatggcg ttagtatgag tgtcgtgcag cctccaggac    120
ccccctccc gggagagcca tagtggtctg cggaaccggt gagtacaccg gaattgccag     180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc ccccccctaa cgttactggc   1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgaccctttg caggcagcgg   1500
aacccccac ctggcgacag gtgcctctgc ggccaaaagc cacgtgtata agatacacct    1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacggccta ctcccaacag acgcgaggcc tacttggctg catcatcact   1860
agcctcacag gccgggacag gaaccaggtc gagggggagg tccaagtggt ctccaccgca   1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagctcgg acctttactt ggtcacgagg catgccgatg tcattccggt gcgccggcgg   2160
ggcgacagca gggggagcct actctccccc aggcccgtct cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtacccgtcg agtctatgga aaccactatg   2340
cggtccccgg tcttcacgga caactcgtcc cctccggccg taccgcagac attccaggtg   2400
```

-continued

```
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatggcaagt ttcttgccga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880
aagggggggga ggcacctcat tttctgccat tccaagaaga aatgtgatga gctcgccgcg   2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gcccctgctg   3600
tataggctgg gagccgttca aaacgaggtt actaccacac accccataac caaatacatc   3660
atggcatgca tgtcggctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtccttta ccgggagttc   3840
gatgagatgg aagagtgcgc ctcacacctc ccttacatcg aacagggaat gcagctcgcc   3900
gaacaattca aacagaaggc aatcgggttg ctgcaaacag ccaccaagca agcggaggct   3960
gctgctcccg tggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgccctcc accgaggacc tggttaacct actccctgct   4380
atcctctccc ctggcgccct agtcgtcggg gtcgtgtgcg cagcgatact gcgtcggcac   4440
gtgggcccag gggagggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
```

-continued

```
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtgggggatt tccactacgt gacgggcatg   5040
accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgacccct cccacattac ggcggagacg   5280
gctaagcgta ggctggccag gggatctccc ccctccttgg ccagctcatc agctagccag   5340
ctgtctgcgc cttccttgaa ggcaacatgc actacccgtc atgactcccc ggacgctgac   5400
ctcatcgagg ccaacctcct gtggcggcag gagatgggcg ggaacatcac ccgcgtggag   5460
tcagaaaata aggtagtaat tttggactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cgggtgtcca ttgccgcctg ccaaggcccc tccgatacca   5700
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc ccccccttga gggggagccg ggggatcccg atctcagcga cgggtcttgg   5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tggggcaaag   6300
gacgtccgga acctatccag caaggccgtt aaccacatcc gctccgtgtg gaaggacttg   6360
ctggaagaca ctgagacacc aattgacacc accatcatgg caaaaaatga ggttttctgc   6420
gtccaaccag agaagggggg ccgcaagcca gctcgcctta tcgtattccc agatttgggg   6480
gttcgtgtgt gcgagaaaat ggccctttac gatgtggtct ccaccctccc tcaggccgtg   6540
atgggctctt catacggatt ccaatactct cctggacagc gggtcgagtt cctggtgaat   6600
gcctggaaag cgaagaaatg ccctatgggc ttcgcatatg acacccgctg ttttgactca   6660
acggtcactg agaatgacat ccgtgttgag gagtcaatct accaatgttg tgacttggcc   6720
cccgaagcca gacaggccat aaggtcgctc acagagcggc tttacatcgg gggcccccctg  6780
actaattcta aagggcagaa ctgcggctat cgccggtgcc gcgcgagcgg tgtactgacg   6840
accagctgcg gtaataccct cacatgttac ttgaaggccg ctgcggcctg tcgagctgcg   6900
aagctccagg actgcacgat gctcgtatgc ggagacgacc ttgtcgttat ctgtgaaagc   6960
gcggggaccc aagaggacga ggcgagccta cgggccttca cggaggctat gactagatac   7020
tctgcccccc ctggggaccc gcccaaacca gaatacgact tggagttgat aacatcatgc   7080
tcctccaatg tgtcagtcgc gcacgatgca tctggcaaaa gggtgtacta tctcacccgt   7140
gaccccacca ccccccttgc gcgggctgcg tgggagacag ctagacacac tccagtcaat   7200
```

-continued tcctggctag gcaacatcat catgtatgcg cccaccttgt gggcaaggat gatcctgatg 7260
actcatttct tctccatcct tctagctcag gaacaacttg aaaaagccct agattgtcag 7320
atctacgggg cctgttactc cattgagcca cttgacctac ctcagatcat tcaacgactc 7380
catggcctta gcgcattttc actccatagt tactctccag gtgagatcaa tagggtggct 7440
tcatgcctca ggaaacttgg ggtaccgccc ttgcgagtct ggagacatcg ggccagaagt 7500
gtccgcgcta ggctactgtc ccaggggggg agggctgcca cttgtggcaa gtacctcttc 7560
aactgggcag taaggaccaa gctcaaactc actccaatcc cggctgcgtc ccagttggat 7620
ttatccagct ggttcgttgc tggttacagc gggggagaca tatatcacag cctgtctcgt 7680
gcccgacccc gctggttcat gtggtgccta ctcctacttt ctgtaggggt aggcatctat 7740
ctactcccca accgatgaac ggggagctaa acactccagg ccaataggcc atcctgtttt 7800
tttccctttt tttttttctt tttttttttt tttttttttt tttttttttt ttctcctttt 7860
tttttcctct tttttccttt ttctttcctt tggtggctcc atcttagccc tagtcacggc 7920
tagctgtgaa aggtccgtga gccgcttgac tgcagagagt gctgatactg gcctctctgc 7980
agatcaagt 7989

<210> SEQ ID NO 2
<211> LENGTH: 8024
<212> TYPE: DNA
<213> ORGANISM: Hepatitis C virus

<400> SEQUENCE: 2
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacaa atcctaaacc 360
tcaaagaaaa accaaaagaa acaccaaccg tcgcccaatg attgaacaag atggattgca 420
cgcaggttct ccggccgctt gggtggagag gctattcggc tatgactggg cacaacagac 480
aatcggctgc tctgatgccg ccgtgttccg gctgtcagcg caggggcgcc cggttctttt 540
tgtcaagacc gacctgtccg gtgccctgaa tgaactgcag gacgaggcag cgcggctatc 600
gtggctggcc acgacgggcg ttccttgcgc agctgtgctc gacgttgtca ctgaagcggg 660
aagggactgg ctgctattgg gcgaagtgcc ggggcaggat ctcctgtcat ctcaccttgc 720
tcctgccgag aaagtatcca tcatggctga tgcaatgcgg cggctgcata cgcttgatcc 780
ggctacctgc ccattcgacc accaagcgaa acatcgcatc gagcgagcac gtactcggat 840
ggaagccggt cttgtcgatc aggatgatct ggacgaagag catcaggggc tcgcgccagc 900
cgaactgttc gccaggctca aggcgcgcat gcccgacggc gaggatctcg tcgtgaccca 960
tggcgatgcc tgcttgccga atatcatggt ggaaaatggc cgcttttctg gattcatcga 1020
ctgtggccgg ctgggtgtgg cggaccgcta tcaggacata gcgttggcta cccgtgatat 1080
tgctgaagag cttggcggcg aatgggctga ccgcttcctc gtgctttacg gtatcgccgc 1140
tcccgattcg cagcgcatcg ccttctatcg ccttcttgac gagttcttct gagtttaaac 1200
cctctccctc ccccccccct aacgttactg gccgaagccg cttggaataa ggccggtgtg 1260
cgtttgtcta tatgttattt tccaccatat tgccgtcttt tggcaatgtg agggcccgga 1320

-continued

```
aacctggccc tgtcttcttg acgagcattc ctaggggtct ttcccctctc gccaaaggaa   1380
tgcaaggtct gttgaatgtc gtgaaggaag cagttcctct ggaagcttct tgaagacaaa   1440
caacgtctgt agcgaccctt tgcaggcagc ggaacccccc acctggcgac aggtgcctct   1500
gcggccaaaa gccacgtgta taagatacac ctgcaaaggc ggcacaaccc cagtgccacg   1560
ttgtgagttg gatagttgtg gaaagagtca aatggctctc ctcaagcgta ttcaacaagg   1620
ggctgaagga tgcccagaag gtaccccatt gtatgggatc tgatctgggg cctcggtgca   1680
catgctttac atgtgtttag tcgaggttaa aaaaacgtct aggccccccg aaccacgggg   1740
acgtggtttt cctttgaaaa acacgatgat accatggctc ccatcactgc ttatgcccag   1800
caaacacgag gcctcctggg cgccatagtg gtgagtatga cggggcgtga caggacagaa   1860
caggccgggg aagtccaaat cctgtccaca gtctctcagt ccttcctcgg aacaaccatc   1920
tcgggggttt tgtggactgt ttaccacgga gctggcaaca agactctagc cggcttacgg   1980
ggtccggtca cgcagatgta ctcgagtgct gaggggggact tggtaggctg gcccagcccc   2040
cctgggacca agtctttgga gccgtgcaag tgtggagccg tcgacctata tctggtcacg   2100
cggaacgctg atgtcatccc ggctcggaga cgcggggaca agcggggagc attgctctcc   2160
ccgagaccca tttcgacctt gaaggggtcc tcggggggggc cggtgctctg ccctaggggc   2220
cacgtcgttg ggctcttccg agcagctgtg tgctctcggg gcgtggccaa atccatcgat   2280
ttcatccccg ttgagacact cgacgttgtt acaaggtctc ccactttcag tgacaacagc   2340
acgccaccgg ctgtgcccca gacctatcag gtcgggtact tgcatgctcc aactggcagt   2400
ggaaagagca ccaaggtccc tgtcgcgtat gccgcccagg ggtacaaagt actagtgctt   2460
aacccctcgg tagctgccac cctggggttt ggggcgtacc tatccaaggc acatggcatc   2520
aatcccaaca ttaggactgg agtcaggacc gtgatgaccg gggaggccat cacgtactcc   2580
acatatggca aatttctcgc cgatgggggc tgcgctagcg gcgcctatga catcatcata   2640
tgcgatgaat gccacgctgt ggatgctacc tccattctcg gcatcggaac ggtccttgat   2700
caagcagaga cagccggggt cagactaact gtgctggcta cggccacacc ccccgggtca   2760
gtgacaaccc cccatcccga tatagaagag gtaggcctcg ggcgggaggg tgagatcccc   2820
ttctatggga gggcgattcc cctatcctgc atcaagggag ggagacacct gattttctgc   2880
cactcaaaga aaaagtgtga cgagctcgcg gcggcccttc ggggcatggg cttgaatgcc   2940
gtggcatact atagagggtt ggacgtctcc ataataccag ctcagggaga tgtggtggtc   3000
gtcgccaccg acgccctcat gacggggtac actggagact ttgactccgt gatcgactgc   3060
aatgtagcgg tcacccaagc tgtcgacttc agcctggacc ccaccttcac tataaccaca   3120
cagactgtcc cacaagacgc tgtctcacgc agtcagcgcc gcgggcgcac aggtagagga   3180
agacagggca cttataggta tgtttccact ggtgaacgag cctcaggaat gtttgacagt   3240
gtagtgcttt gtgagtgcta cgacgcaggg gctgcgtggt acgatctcac accagcggag   3300
accaccgtca ggcttagagc gtatttcaac acgcccggcc tacccgtgtg tcaagaccat   3360
cttgaatttt gggaggcagt tttcaccggc ctcacacaca tagacgccca cttcctctcc   3420
caaacaaagc aagcgggggga gaacttcgcg tacctagtag cctaccaagc tacggtgtgc   3480
gccagagcca aggcccctcc cccgtcctgg gacgccatgt ggaagtgcct ggcccgactc   3540
aagcctacgc ttgcgggccc cacacctctc ctgtaccgtt tgggccctat taccaatgag   3600
gtcaccctca cacaccctgg gacgaagtac atcgccacat gcatgcaagc tgaccttgag   3660
gtcatgacca gcacgtgggt cctagctgga ggagtcctgg cagccgtcgc cgcatattgc   3720
```

-continued

```
ctggcgactg gatgcgtttc catcatcggc cgcttgcacg tcaaccagcg agtcgtcgtt   3780
gcgccggata aggaggtcct gtatgaggct tttgatgaga tggaggaatg cgcctctagg   3840
gcggctctca tcgaagaggg gcagcggata gccgagatgt tgaagtccaa gatccaaggc   3900
ttgctgcagc aggcctctaa gcaggcccag gacatacaac ccgctatgca ggcttcatgg   3960
cccaaagtgg aacaattttg ggccagacac atgtggaact tcattagcgg catccaatac   4020
ctcgcaggat tgtcaacact gccagggaac cccgcggtgg cttccatgat ggcattcagt   4080
gccgccctca ccagtccgtt gtcgaccagt accaccatcc ttctcaacat catgggaggc   4140
tggttagcgt cccagatcgc accacccgcg ggggccaccg gctttgtcgt cagtggcctg   4200
gtgggggctg ccgtgggcag cataggcctg ggtaaggtgc tggtggacat cctggcagga   4260
tatggtgcgg gcatttcggg ggccctcgtc gcattcaaga tcatgtctgg cgagaagccc   4320
tctatggaag atgtcatcaa tctactgcct gggatcctgt ctccgggagc cctggtggtg   4380
ggggtcatct gcgcggccat tctgcgccgc cacgtgggac cgggggaggg cgcggtccaa   4440
tggatgaaca ggcttattgc ctttgcttcc agaggaaacc acgtcgcccc tactcactac   4500
gtgacggagt cggatgcgtc gcagcgtgtg acccaactac ttggctctct tactataacc   4560
agcctactca gaagactcca caattggata actgaggact gccccatccc atgctccgga   4620
tcctggctcc gcgacgtgtg ggactgggtt tgcaccatct tgacagactt caaaaattgg   4680
ctgacctcta aattgttccc caagctgccc ggcctcccct tcatctcttg tcaaaagggg   4740
tacaagggtg tgtgggccgg cactggcatc atgaccacgc gctgcccttg cggcgccaac   4800
atctctggca atgtccgcct gggctctatg aggatcacag ggcctaaaac ctgcatgaac   4860
acctggcagg ggacctttcc tatcaattgc tacacggagg gccagtgcgc gccgaaaccc   4920
cccacgaact acaagaccgc catctggagg gtggcggcct cggagtacgc ggaggtgacg   4980
cagcatgggt cgtactccta tgtaacagga ctgaccactg acaatctgaa aattccttgc   5040
caactacctt ctccagagtt tttctcctgg gtggacggtg tgcagatcca taggtttgca   5100
cccacaccaa agccgttttt ccgggatgag gtctcgttct gcgttgggct taattcctat   5160
gctgtcgggt cccagcttcc ctgtgaacct gagcccgacg cagacgtatt gaggtccatg   5220
ctaacagatc cgccccacat cacggcggag actgcggcgc ggcgcttggc acggggatca   5280
cctccatctg aggcgagctc ctcagtgagc cagctatcag caccgtcgct gcgggccacc   5340
tgcaccaccc acagcaacac ctatgacgtg gacatggtcg atgccaacct gctcatggag   5400
ggcggtgtgg ctcagacaga gcctgagtcc agggtgcccg ttctggactt tctcgagcca   5460
atggccgagg aagagagcga ccttgagccc tcaataccat cggagtgcat gctccccagg   5520
agcgggtttc cacgggcctt accggcttgg gcacggcctg actacaaccc gccgctcgtg   5580
gaatcgtgga ggaggccaga ttaccaaccg cccaccgttg ctggttgtgc tctccccccc   5640
cccaagaagg ccccgacgcc tcccccaagg agacgccgga cagtgggtct gagcgagagc   5700
accatatcag aagccctcca gcaactggcc atcaagacct ttggccagcc cccctcgagc   5760
ggtgatgcag gctcgtccac gggggcgggc gccgccgaat ccggcggtcc gacgtcccct   5820
ggtgagccgg ccccctcaga gacaggttcc gcctcctcta tgcccccct cgagggggag   5880
cctggagatc cggacctgga gtctgatcag gtagagcttc aacctccccc ccaggggggg   5940
ggggtagctc ccggttcggg ctcggggtct tggtctactt gctccgagga ggacgatacc   6000
accgtgtgct gctccatgtc atactcctgg accggggctc taataactcc ctgtagcccc   6060
gaagaggaaa agttgccaat caaccctttg agtaactcgc tgttgcgata ccataacaag   6120
```

```
gtgtactgta caacatcaaa gagcgcctca cagagggcta aaaaggtaac ttttgacagg   6180

acgcaagtgc tcgacgccca ttatgactca gtcttaaagg acatcaagct agcggcttcc   6240

aaggtcagcg caaggctcct caccttggag gaggcgtgcc agttgactcc accccattct   6300

gcaagatcca agtatggatt cggggccaag gaggtccgca gcttgtccgg gagggccgtt   6360

aaccacatca agtccgtgtg gaaggacctc ctggaagacc cacaaacacc aattcccaca   6420

accatcatgg ccaaaaatga ggtgttctgc gtggaccccg ccaagggggg taagaaacca   6480

gctcgcctca tcgtttaccc tgacctcggc gtccgggtct gcgagaaaat ggccctctat   6540

gacattacac aaaagcttcc tcaggcggta atgggagctt cctatggctt ccagtactcc   6600

cctgcccaac gggtggagta tctcttgaaa gcatgggcgg aaaagaagga ccccatgggt   6660

ttttcgtatg atacccgatg cttcgactca accgtcactg agagagacat caggaccgag   6720

gagtccatat accaggcctg ctccctgccc gaggaggccc gcactgccat acactcgctg   6780

actgagagac tttacgtagg agggcccatg ttcaacagca agggtcaaac ctgcggttac   6840

agacgttgcc gcgccagcgg ggtgctaacc actagcatgg gtaacaccat cacatgctat   6900

gtgaaagccc tagcggcctg caaggctgcg gggatagttg cgcccacaat gctggtatgc   6960

ggcgatgacc tagtagtcat ctcagaaagc caggggactg aggaggacga gcggaacctg   7020

agagccttca cggaggccat gaccaggtac tctgcccctc ctggtgatcc ccccagaccg   7080

gaatatgacc tggagctaat aacatcctgt tcctcaaatg tgtctgtggc gttgggcccg   7140

cggggccgcc gcagatacta cctgaccaga gacccaacca ctccactcgc ccgggctgcc   7200

tgggaaacag ttagacactc ccctatcaat tcatggctgg gaaacatcat ccagtatgct   7260

ccaaccatat gggttcgcat ggtcctaatg acacacttct tctccattct catggtccaa   7320

gacaccctgg accagaacct caactttgag atgtatggat cagtatactc cgtgaatcct   7380

ttggaccttc cagccataat tgagaggtta cacgggcttg acgccttttc tatgcacaca   7440

tactctcacc acgaactgac gcgggtggct tcagccctca gaaaacttgg ggcgccaccc   7500

ctcagggtgt ggaagagtcg ggctcgcgca gtcagggcgt ccctcatctc ccgtggaggg   7560

aaagcggccg tttgcggccg atatctcttc aattgggcgg tgaagaccaa gctcaaactc   7620

actccattgc cggaggcgcg cctactggac ttatccagtt ggttcaccgt cggcgccggc   7680

gggggcgaca tttttcacag cgtgtcgcgc gcccgacccc gctcattact cttcggccta   7740

ctcctacttt tcgtaggggt aggcctcttc ctactccccg ctcggtagag cggcacacac   7800

taggtacact ccatagctaa ctgttccttt tttttttttt tttttttttt tttttttttt   7860

tttttttttt cttttttttt tttttccctc tttcttccct tctcatctta ttctactttc   7920

tttcttggtg gctccatctt agccctagtc acggctagct gtgaaaggtc cgtgagccgc   7980

atgactgcag agagtgccgt aactggtctc tctgcagatc atgt                    8024
```

<210> SEQ ID NO 3
<211> LENGTH: 8001
<212> TYPE: DNA
<213> ORGANISM: Hepatitis C virus

<400> SEQUENCE: 3

```
gccagccccc gattgggggc gacactccac catagatcac tcccctgtga ggaactactg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag    180

gacgaccggg tcctttcttg gatcaacccg ctcaatgcct ggagatttgg gcgtgccccc    240
```

-continued

```
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacg ggcgcgccat gattgaacaa gatggattgc    420
acgcaggttc tccggccgct tgggtggaga ggctattcgg ctatgactgg gcacaacaga    480
caatcggctg ctctgatgcc gccgtgttcc ggctgtcagc gcaggggcgc ccggttcttt    540
ttgtcaagac cgacctgtcc ggtgccctga atgaactgca ggacgaggca gcgcggctat    600
cgtggctggc cacgacgggc gttccttgcg cagctgtgct cgacgttgtc actgaagcgg    660
gaagggactg gctgctattg ggcgaagtgc cggggcagga tctcctgtca tctcaccttg    720
ctcctgccga gaaagtatcc atcatggctg atgcaatgcg gcggctgcat acgcttgatc    780
cggctacctg cccattcgac caccaagcga aacatcgcat cgagcgagca cgtactcgga    840
tggaagccgg tcttgtcgat caggatgatc tggacgaaga gcatcagggg ctcgcgccag    900
ccgaactgtt cgccaggctc aaggcgcgca tgcccgacgg cgaggatctc gtcgtgaccc    960
atggcgatgc ctgcttgccg aatatcatgg tggaaaatgg ccgcttttct ggattcatcg   1020
actgtggccg gctgggtgtg gcggaccgct atcaggacat agcgttggct acccgtgata   1080
ttgctgaaga gcttggcggc gaatgggctg accgcttcct cgtgctttac ggtatcgccg   1140
ctcccgattc gcagcgcatc gccttctatc gccttcttga cgagttcttc tgagtttaaa   1200
cagaccacaa cggtttccct ctagcgggat caattccgcc cctctccctc ccccccccct   1260
aacgttactg gccgaagccg cttggaataa ggccggtgtg cgtttgtcta tatgttattt   1320
tccaccatat tgccgtcttt tggcaatgtg agggcccgga aacctggccc tgtcttcttg   1380
acgagcattc ctaggggtct ttcccctctc gccaaaggaa tgcaaggtct gttgaatgtc   1440
gtgaaggaag cagttcctct ggaagcttct tgaagacaaa caacgtctgt agcgaccctt   1500
tgcaggcagc ggaacccccc acctggcgac aggtgcctct gcggccaaaa gccacgtgta   1560
taagatacac ctgcaaaggc ggcacaaccc cagtgccacg ttgtgagttg gatagttgtg   1620
gaaagagtca aatggctctc ctcaagcgta ttcaacaagg ggctgaagga tgcccagaag   1680
gtaccccatt gtatgggatc tgatctgggg cctcggtgca catgctttac atgtgtttag   1740
tcgaggttaa aaaacgtcta ggccccccga accacgggga cgtggttttc ctttgaaaaa   1800
cacgataata ccatggcgcc tattacggcc tactcccaac agacgcgagg cctacttggc   1860
tgcatcatca ctagcctcac aggccgggac aggaaccagg tcgaggggga ggtccaagtg   1920
gtctccaccg caacacaatc tttcctggcg acctgcgtca atggcgtgtg ttggactgtc   1980
tatcatggtg ccggctcaaa gacccttgcc ggcccaaagg gcccaatcac ccaaatgtac   2040
accaatgtgg accaggacct cgtcggctgg caagcgcccc ccggggcgcg ttccttgaca   2100
ccatgcacct gcggcagctc ggacctttac ttggtcacga ggcatgccga tgtcattccg   2160
gtgcgccggc ggggcgacag caggggggagc ctactctccc ccaggcccgt ctcctacttg   2220
aagggctctt cgggcggtcc actgctctgc ccctcggggc acgctgtggg catctttcgg   2280
gctgccgtgt gcacccgagg ggttgcgaag gcggtggact ttgtacccgt cgagtctatg   2340
gaaaccacta tgcggtcccc ggtcttcacg gacaactcgt cccctccggc cgtaccgcag   2400
acattccagg tggcccatct acacgcccct actggtagcg gcaagagcac taaggtgccg   2460
gctgcgtatg cagcccaagg gtataaggtg cttgtcctga acccgtccgt cgccgccacc   2520
ctaggtttcg ggcgtatat gtctaaggca catggtatcg accctaacat cagaaccggg   2580
gtaaggacca tcaccacggg tgcccccatc acgtactcca cctatggcaa gtttcttgcc   2640
```

-continued

```
gacggtggtt gctctggggg cgcctatgac atcataatat gtgatgagtg ccactcaact   2700
gactcgacca ctatcctggg catcggcaca gtcctggacc aagcggagac ggctggagcg   2760
cgactcgtcg tgctcgccac cgctacgcct ccgggatcgg tcaccgtgcc acatccaaac   2820
atcgaggagg tggctctgtc cagcactgga gaaatcccct tttatggcaa agccatcccc   2880
atcgagacca tcaagggggg gaggcacctc attttctgcc attccaagaa gaaatgtgat   2940
gagctcgccg cgaagctgtc cggcctcgga ctcaatgctg tagcatatta ccggggcctt   3000
gatgtatccg tcataccaac tagcggagac gtcattgtcg tagcaacgga cgctctaatg   3060
acgggcttta ccggcgattt cgactcagtg atcgactgca atacatgtgt cacccagaca   3120
gtcgacttca gcctggaccc gaccttcacc attgagacga cgaccgtgcc acaagacgcg   3180
gtgtcacgct cgcagcggcg aggcaggact ggtaggggca ggatgggcat ttacaggttt   3240
gtgactccag gagaacggcc ctcgggcatg ttcgattcct cggttctgtg cgagtgctat   3300
gacgcgggct gtgcttggta cgagctcacg cccgccgaga cctcagttag gttgcgggct   3360
tacctaaaca caccagggtt gcccgtctgc caggaccatc tggagttctg ggagagcgtc   3420
tttacaggcc tcacccacat agacgcccat ttcttgtccc agactaagca ggcaggagac   3480
aacttcccct acctggtagc ataccaggct acggtgtgcg ccagggctca ggctccacct   3540
ccatcgtggg accaaatgtg gaagtgtctc atacggctaa agcctacgct gcacgggcca   3600
acgcccctgc tgtataggct gggagccgtt caaaacgagg ttactaccac acaccccata   3660
accaaataca tcatggcatg catgtcggct gacctggagg tcgtcacgag cacctgggtg   3720
ctggtaggcg gagtcctagc agctctggcc gcgtattgcc tgacaacagg cagcgtggtc   3780
attgtgggca ggatcatctt gtccggaaag ccggccatca ttcccgacag ggaagtcctt   3840
taccgggagt tcgatgagat ggaagagtgc gcctcacacc tcccttacat cgaacaggga   3900
atgcagctcg ccgaacaatt caaacagaag gcaatcgggt tgctgcaaac agccaccaag   3960
caagcggagg ctgctgctcc cgtggtggaa tccaagtggc ggaccctcga agccttctgg   4020
gcgaagcata tgtggaattt catcagcggg atacaatatt tagcaggctt gtccactctg   4080
cctggcaacc ccgcgatagc atcactgatg gcattcacag cctctatcac cagcccgctc   4140
accacccaac ataccctcct gtttaacatc ctgggggggat gggtggccgc ccaacttgct   4200
cctcccagcg ctgcttctgc tttcgtaggc gccggcatcg ctggagcggc tgttggcagc   4260
ataggccttg ggaaggtgct tgtggatatt ttggcaggtt atggagcagg ggtggcaggc   4320
gcgctcgtgg cctttaaggt catgagcggc gagatgccct ccaccgagga cctggttaac   4380
ctactccctg ctatcctctc ccctggcgcc ctagtcgtcg ggtcgtgtg cgcagcgata   4440
ctgcgtcggc acgtgggccc aggggagggg gctgtgcagt ggatgaaccg gctgatagcg   4500
ttcgcttcgc ggggtaacca cgtctccccc acgcactatg tgcctgagag cgacgctgca   4560
gcacgtgtca ctcagatcct ctctagtctt accatcactc agctgctgaa gaggcttcac   4620
cagtggatca acgaggactg ctccacgcca tgctccggct cgtggctaag agatgtttgg   4680
gattggatat gcacggtgtt gactgatttc aagacctggc tccagtccaa gctcctgccg   4740
cgattgccgg gagtcccctt cttctcatgt caacgtgggt acaagggagt ctggcggggc   4800
gacggcatca tgcaaaccac ctgcccatgt ggagcacaga tcaccggaca tgtgaaaaac   4860
ggttccatga ggatcgtggg gcctaggacc tgtagtaaca cgtggcatgg aacattcccc   4920
attaacgcgt acaccacggg cccctgcacg ccctccccgg cgccaaatta ttctagggcg   4980
ctgtggcggg tggctgctga ggagtacgtg gaggttacgc gggtggggga tttccactac   5040
```

-continued

```
gtgacgggca tgaccactga caacgtaaag tgcccgtgtc aggttccggc cccgaattc   5100
ttcacagaag tggatggggt gcggttgcac aggtacgctc cagcgtgcaa acccctccta   5160
cgggaggagg tcacattcct ggtcgggctc aatcaatacc tggttgggtc acagctccca   5220
tgcgagcccg aaccggacgt agcagtgctc acttccatgc tcaccgaccc ctcccacatt   5280
acggcggaga cggctaagcg taggctggcc aggggatctc ccccctcctt ggccagctca   5340
tcagctagcc agctgtctgc gccttccttg aaggcaacat gcactacccg tcatgactcc   5400
ccggacgctg acctcatcga ggccaacctc ctgtggcggc aggagatggg cgggaacatc   5460
acccgcgtgg agtcagaaaa taaggtagta attttggact ctttcgagcc gctccaagcg   5520
gaggaggatg agagggaagt atccgttccg gcggagatcc tgcggaggtc caggaaattc   5580
cctcgagcga tgcccatatg ggcacgcccg gattacaacc ctccactgtt agagtcctgg   5640
aaggacccgg actacgtccc tccagtggta cacgggtgtc cattgccgcc tgccaaggcc   5700
cctccgatac cacctccacg gaggaagagg acggttgtcc tgtcagaatc taccgtgtct   5760
tctgccttgg cggagctcgc cacaaagacc ttcggcagct ccgaatcgtc ggccgtcgac   5820
agcggcacgg caacggcctc tcctgaccag ccctccgacg acggcgacgc gggatccgac   5880
gttgagtcgt actcctccat gccccccctt gaggggggagc cgggggatcc cgatctcagc   5940
gacgggtctt ggtctaccgt aagcgaggag gctagtgagg acgtcgtctg ctgctcgatg   6000
tcctacacat ggacaggcgc cctgatcacg ccatgcgctg cggaggaaac caagctgccc   6060
atcaatgcac tgagcaactc tttgctccgt caccacaact tggtctatgc tacaacatct   6120
cgcagcgcaa gcctgcggca gaagaaggtc acctttgaca gactgcaggt cctggacgac   6180
cactaccggg acgtgctcaa ggagatgaag gcgaaggcgt ccacagttaa ggctaaactt   6240
ctatccgtgg aggaagcctg taagctgacg cccccacatt cggccagatc taaatttggc   6300
tatggggcaa aggacgtccg gaacctatcc agcaaggccg ttaaccacat ccgctccgtg   6360
tggaaggact tgctggaaga cactgagaca ccaattgaca ccaccatcat ggcaaaaaat   6420
gaggttttct gcgtccaacc agagaagggg ggccgcaagc cagctcgcct tatcgtattc   6480
ccagatttgg gggttcgtgt gtgcgagaaa atggcccttt acgatgtggt ctccaccctc   6540
cctcaggccg tgatgggctc ttcatacgga ttccaatact ctcctggaca gcgggtcgag   6600
ttcctggtga atgcctggaa agcgaagaaa tgccctatgg gcttcgcata tgacacccgc   6660
tgttttgact caacggtcac tgagaatgac atccgtgttg aggagtcaat ctaccaatgt   6720
tgtgacttgg cccccgaagc cagacaggcc ataaggtcgc tcacagagcg gctttacatc   6780
gggggccccc tgactaattc taaagggcag aactgcggct atcgccggtg ccgcgcgagc   6840
ggtgtactga cgaccagctg cggtaatacc ctcacatgtt acttgaaggc cgctgcggcc   6900
tgtcgagctg cgaagctcca ggactgcacg atgctcgtat gcggagacga ccttgtcgtt   6960
atctgtgaaa gcgcggggac ccaagaggac gaggcgagcc tacgggcctt cacggaggct   7020
atgactagat actctgcccc ccctggggac ccgcccaaac cagaatacga cttggagttg   7080
ataacatcat gctcctccaa tgtgtcagtc gcgcacgatg catctggcaa aagggtgtac   7140
tatctcaccc gtgaccccac cacccccctt gcgcgggctg cgtgggagac agctagacac   7200
actccagtca attcctggct aggcaacatc atcatgtatg cgcccacctt gtgggcaagg   7260
atgatcctga tgactcattt cttctccatc cttctagctc aggaacaact tgaaaaagcc   7320
ctagattgtc agatctacgg ggcctgttac tccattgagc cacttgacct acctcagatc   7380
attcaacgac tccatggcct tagcgcattt tcactccata gttactctcc aggtgagatc   7440
```

-continued

```
aatagggtgg cttcatgcct caggaaactt ggggtaccgc ccttgcgagt ctggagacat   7500

cgggccagaa gtgtccgcgc taggctactg tcccaggggg ggagggctgc cacttgtggc   7560

aagtacctct tcaactgggc agtaaggacc aagctcaaac tcactccaat cccggctgcg   7620

tcccagttgg atttatccag ctggttcgtt gctggttaca gcgggggaga catatatcac   7680

agcctgtctc gtgcccgacc ccgctggttc atgtggtgcc tactcctact ttctgtaggg   7740

gtaggcatct atctactccc caaccgatga acggggagct aaacactcca ggccaatagg   7800

ccatcctgtt tttttccctt ttttttttc ttttttttt ttttttttt ttttttttt       7860

ttttctcctt tttttttcct cttttttcc ttttctttcc tttggtggct ccatcttagc     7920

cctagtcacg gctagctgtg aaaggtccgt gagccgcttg actgcagaga gtgctgatac   7980

tggcctctct gcagatcaag t                                             8001
```

<210> SEQ ID NO 4
<211> LENGTH: 8649
<212> TYPE: DNA
<213> ORGANISM: Hepatitis C virus

<400> SEQUENCE: 4

```
gccagccccc gattgggggc gacactccac catagatcac tcccctgtga ggaactactg     60

tcttcacgca gaaagcgtct agccatggcg ttagtatgag tgtcgtgcag cctccaggac    120

ccccctccc gggagagcca tagtggtctg cggaaccggt gagtacaccg gaattgccag     180

gacgaccggg tcctttcttg gatcaacccg ctcaatgcct ggagatttgg gcgtgccccc    240

gcgagactgc tagccgagta gtgttgggtc gcgaaaggcc ttgtggtact gcctgatagg    300

gtgcttgcga gtgccccggg aggtctcgta gaccgtgcac catgagcacg aatcctaaac    360

ctcaaagaaa aaccaaacgt aacaccaacg ggcgcgccat gattgaacaa gatggattgc    420

acgcaggttc tccggccgct tgggtggaga ggctattcgg ctatgactgg gcacaacaga    480

caatcggctg ctctgatgcc gccgtgttcc ggctgtcagc gcaggggcgc ccggttcttt    540

ttgtcaagac cgacctgtcc ggtgccctga atgaactgca ggacgaggca gcgcggctat    600

cgtggctggc cacgacgggc gttccttgcg cagctgtgct cgacgttgtc actgaagcgg    660

gaagggactg gctgctattg ggcgaagtgc cggggcagga tctcctgtca tctcaccttg    720

ctcctgccga gaaagtatcc atcatggctg atgcaatgcg gcggctgcat acgcttgatc    780

cggctacctg cccattcgac caccaagcga aacatcgcat cgagcgagca cgtactcgga    840

tggaagccgg tcttgtcgat caggatgatc tggacgaaga gcatcagggg ctcgcgccag    900

ccgaactgtt cgccaggctc aaggcgcgca tgcccgacgg cgaggatctc gtcgtgaccc    960

atggcgatgc ctgcttgccg aatatcatgg tggaaaatgg ccgcttttct ggattcatcg   1020

actgtggccg gctgggtgtg gcggaccgct atcaggacat agcgttggct acccgtgata   1080

ttgctgaaga gcttggcggc gaatgggctg accgcttcct cgtgctttac ggtatcgccg   1140

ctcccgattc gcagcgcatc gccttctatc gccttcttga cgagttcttc tgagtttaaa   1200

cagaccacaa cggtttccct ctagcgggat caattccgcc cctctccctc cccccccct    1260

aacgttactg gccgaagccg cttggaataa ggccggtgtg cgtttgtcta tatgttattt   1320

tccaccatat tgccgtcttt tggcaatgtg agggcccgga aacctggccc tgtcttcttg   1380

acgagcattc ctaggggtct ttcccctctc gccaaaggaa tgcaaggtct gttgaatgtc   1440

gtgaaggaag cagttcctct ggaagcttct tgaagacaaa caacgtctgt agcgaccctt   1500

tgcaggcagc ggaacccccc acctggcgac aggtgcctct gcggccaaaa gccacgtgta   1560
```

-continued

```
taagatacac ctgcaaaggc ggcacaaccc cagtgccacg ttgtgagttg gatagttgtg   1620
gaaagagtca aatggctctc ctcaagcgta ttcaacaagg ggctgaagga tgcccagaag   1680
gtaccccatt gtatgggatc tgatctgggg cctcggtgca catgctttac atgtgtttag   1740
tcgaggttaa aaaacgtcta ggccccccga accacgggga cgtggttttc ctttgaaaaa   1800
cacgataata ccatggaccg ggagatggca gcatcgtgcg gaggcgcggt tttcgtaggt   1860
ctgatactct tgaccttgtc accgcactat aagctgttcc tcgctaggct catatggtgg   1920
ttacaatatt ttatcaccag ggccgaggca cacttgcaag tgtggatccc ccccctcaac   1980
gttcgggggg gccgcgatgc cgtcatcctc ctcacgtgcg cgatccaccc agagctaatc   2040
tttaccatca ccaaaatctt gctcgccata ctcggtccac tcatggtgct ccaggctggt   2100
ataaccaaag tgccgtactt cgtgcgcgca cacgggctca ttcgtgcatg catgctggtg   2160
cggaaggttg ctgggggtca ttatgtccaa atggctctca tgaagttggc cgcactgaca   2220
ggtacgtacg tttatgacca tctcacccca ctgcgggact gggcccacgc gggcctacga   2280
gaccttgcgg tggcagttga gcccgtcgtc ttctctgata tggagaccaa ggttatcacc   2340
tggggggcag acaccgcggc gtgtggggac atcatcttgg gcctgcccgt ctccgcccgc   2400
agggggaggg agatacatct gggaccggca gacagccttg aagggcaggg gtggcgactc   2460
ctcgcgccta ttacggccta ctcccaacag acgcgaggcc tacttggctg catcatcact   2520
agcctcacag gccgggacag gaaccaggtc gagggggagg tccaagtggt ctccaccgca   2580
acacaatctt tcctggcgac ctgcgtcaat ggcgtgtgtt ggactgtcta tcatggtgcc   2640
ggctcaaaga cccttgccgg cccaaagggc ccaatcaccc aaatgtacac caatgtggac   2700
caggacctcg tcggctggca agcgcccccc ggggcgcgtt ccttgacacc atgcacctgc   2760
ggcagctcgg acctttactt ggtcacgagg catgccgatg tcattccggt gcgccggcgg   2820
ggcgacagca gggggagcct actctccccc aggcccgtct cctacttgaa gggctcttcg   2880
ggcggtccac tgctctgccc ctcggggcac gctgtgggca tctttcgggc tgccgtgtgc   2940
acccgagggg ttgcgaaggc ggtggacttt gtacccgtcg agtctatgga aaccactatg   3000
cggtccccgg tcttcacgga caactcgtcc cctccggccg taccgcagac attccaggtg   3060
gcccatctac acgcccctac tggtagcggc aagagcacta aggtgccggc tgcgtatgca   3120
gcccaagggt ataaggtgct tgtcctgaac ccgtccgtcg ccgccaccct aggtttcggg   3180
gcgtatatgt ctaaggcaca tggtatcgac cctaacatca gaaccggggt aaggaccatc   3240
accacgggtg cccccatcac gtactccacc tatggcaagt ttcttgccga cggtggttgc   3300
tctgggggcg cctatgacat cataatatgt gatgagtgcc actcaactga ctcgaccact   3360
atcctgggca tcggcacagt cctggaccaa gcggagacgg ctggagcgcg actcgtcgtg   3420
ctcgccaccg ctacgcctcc gggatcggtc accgtgccac atccaaacat cgaggaggtg   3480
gctctgtcca gcactggaga aatccccttt tatggcaaag ccatccccat cgagaccatc   3540
aaggggggga ggcacctcat ttctgccat tccaagaaga aatgtgatga gctcgccgcg   3600
aagctgtccg gcctcggact caatgctgta gcatattacc ggggccttga tgtatccgtc   3660
ataccaacta gcggagacgt cattgtcgta gcaacggacg ctctaatgac gggctttacc   3720
ggcgatttcg actcagtgat cgactgcaat acatgtgtca cccagacagt cgacttcagc   3780
ctggacccga ccttcaccat tgagacgacg accgtgccac aagacgcggt gtcacgctcg   3840
cagcggcgag gcaggactgg taggggcagg atgggcattt acaggtttgt gactccagga   3900
gaacggccct cgggcatgtt cgattcctcg gttctgtgcg agtgctatga cgcgggctgt   3960
```

-continued

```
gcttggtacg agctcacgcc cgccgagacc tcagttaggt tgcgggctta cctaaacaca   4020

ccagggttgc ccgtctgcca ggaccatctg gagttctggg agagcgtctt tacaggcctc   4080

acccacatag acgcccattt cttgtcccag actaagcagg caggagacaa cttcccctac   4140

ctggtagcat accaggctac ggtgtgcgcc agggctcagg ctccacctcc atcgtgggac   4200

caaatgtgga agtgtctcat acggctaaag cctacgctgc acgggccaac gcccctgctg   4260

tataggctgg gagccgttca aaacgaggtt actaccacac accccataac caaatacatc   4320

atggcatgca tgtcggctga cctggaggtc gtcacgagca cctgggtgct ggtaggcgga   4380

gtcctagcag ctctggccgc gtattgcctg acaacaggca gcgtggtcat tgtgggcagg   4440

atcatcttgt ccggaaagcc ggccatcatt cccgacaggg aagtccttta ccgggagttc   4500

gatgagatgg aagagtgcgc ctcacacctc ccttacatcg aacagggaat gcagctcgcc   4560

gaacaattca aacagaaggc aatcgggttg ctgcaaacag ccaccaagca agcggaggct   4620

gctgctcccg tggtggaatc caagtggcgg accctcgaag ccttctgggc gaagcatatg   4680

tggaatttca tcagcgggat acaatattta gcaggcttgt ccactctgcc tggcaacccc   4740

gcgatagcat cactgatggc attcacagcc tctatcacca gcccgctcac cacccaacat   4800

accctcctgt ttaacatcct gggggggatgg gtggccgccc aacttgctcc tcccagcgct   4860

gcttctgctt tcgtaggcgc cggcatcgct ggagcggctg ttggcagcat aggccttggg   4920

aaggtgcttg tggatatttt ggcaggttat ggagcagggg tggcaggcgc gctcgtggcc   4980

tttaaggtca tgagcggcga gatgccctcc accgaggacc tggttaacct actccctgct   5040

atcctctccc ctggcgccct agtcgtcggg gtcgtgtgcg cagcgatact gcgtcggcac   5100

gtgggcccag gggagggggc tgtgcagtgg atgaaccggc tgatagcgtt cgcttcgcgg   5160

ggtaaccacg tctcccccac gcactatgtg cctgagagcg acgctgcagc acgtgtcact   5220

cagatcctct ctagtcttac catcactcag ctgctgaaga ggcttcacca gtggatcaac   5280

gaggactgct ccacgccatg ctccggctcg tggctaagag atgtttggga ttggatatgc   5340

acggtgttga ctgatttcaa gacctggctc cagtccaagc tcctgccgcg attgccggga   5400

gtccccttct tctcatgtca acgtgggtac aagggagtct ggcggggcga cggcatcatg   5460

caaaccacct gcccatgtgg agcacagatc accggacatg tgaaaaacgg ttccatgagg   5520

atcgtggggc ctaggacctg tagtaacacg tggcatggaa cattccccat taacgcgtac   5580

accacgggcc cctgcacgcc ctccccggcg ccaaattatt ctagggcgct gtggcgggtg   5640

gctgctgagg agtacgtgga ggttacgcgg gtgggggatt tccactacgt gacgggcatg   5700

accactgaca acgtaaagtg cccgtgtcag gttccggccc ccgaattctt cacagaagtg   5760

gatggggtgc ggttgcacag gtacgctcca gcgtgcaaac ccctcctacg ggaggaggtc   5820

acattcctgg tcgggctcaa tcaatacctg gttgggtcac agctcccatg cgagcccgaa   5880

ccggacgtag cagtgctcac ttccatgctc accgacccct cccacattac ggcggagacg   5940

gctaagcgta ggctggccag gggatctccc ccctccttgg ccagctcatc agctagccag   6000

ctgtctgcgc cttccttgaa ggcaacatgc actacccgtc atgactcccc ggacgctgac   6060

ctcatcgagg ccaacctcct gtggcggcag gagatgggcg ggaacatcac ccgcgtggag   6120

tcagaaaata aggtagtaat tttggactct ttcgagccgc tccaagcgga ggaggatgag   6180

agggaagtat ccgttccggc ggagatcctg cggaggtcca ggaaattccc tcgagcgatg   6240

cccatatggg cacgcccgga ttacaaccct ccactgttag agtcctggaa ggacccggac   6300

tacgtccctc cagtggtaca cgggtgtcca ttgccgcctg ccaaggcccc tccgatacca   6360
```

-continued

```
cctccacgga ggaagaggac ggttgtcctg tcagaatcta ccgtgtcttc tgccttggcg    6420
gagctcgcca caaagacctt cggcagctcc gaatcgtcgg ccgtcgacag cggcacggca    6480
acggcctctc ctgaccagcc ctccgacgac ggcgacgcgg gatccgacgt tgagtcgtac    6540
tcctccatgc ccccccttga gggggagccg ggggatcccg atctcagcga cgggtcttgg    6600
tctaccgtaa gcgaggaggc tagtgaggac gtcgtctgct gctcgatgtc ctacacatgg    6660
acaggcgccc tgatcacgcc atgcgctgcg gaggaaacca agctgcccat caatgcactg    6720
agcaactctt tgctccgtca ccacaacttg gtctatgcta caacatctcg cagcgcaagc    6780
ctgcggcaga agaaggtcac ctttgacaga ctgcaggtcc tggacgacca ctaccgggac    6840
gtgctcaagg agatgaaggc gaaggcgtcc acagttaagg ctaaacttct atccgtggag    6900
gaagcctgta agctgacgcc cccacattcg gccagatcta aatttggcta tggggcaaag    6960
gacgtccgga acctatccag caaggccgtt aaccacatcc gctccgtgtg gaaggacttg    7020
ctggaagaca ctgagacacc aattgacacc accatcatgg caaaaaatga ggtttttctgc    7080
gtccaaccag agaagggggg ccgcaagcca gctcgcctta tcgtattccc agatttgggg    7140
gttcgtgtgt gcgagaaaat ggccctttac gatgtggtct ccaccctccc tcaggccgtg    7200
atgggctctt catacggatt ccaatactct cctggacagc gggtcgagtt cctggtgaat    7260
gcctggaaag cgaagaaatg ccctatgggc ttcgcatatg acacccgctg ttttgactca    7320
acggtcactg agaatgacat ccgtgttgag gagtcaatct accaatgttg tgacttggcc    7380
cccgaagcca gacaggccat aaggtcgctc acagagcggc tttacatcgg gggccccctg    7440
actaattcta aagggcagaa ctgcggctat cgccggtgcc gcgcgagcgg tgtactgacg    7500
accagctgcg gtaataccct cacatgttac ttgaaggccg ctgcggcctg tcgagctgcg    7560
aagctccagg actgcacgat gctcgtatgc ggagacgacc ttgtcgttat ctgtgaaagc    7620
gcggggaccc aagaggacga ggcgagccta cgggccttca cggaggctat gactagatac    7680
tctgcccccc ctggggaccc gcccaaacca gaatacgact tggagttgat aacatcatgc    7740
tcctccaatg tgtcagtcgc gcacgatgca tctggcaaaa gggtgtacta tctcacccgt    7800
gaccccacca ccccccttgc gcgggctgcg tgggagacag ctagacacac tccagtcaat    7860
tcctggctag gcaacatcat catgtatgcg cccaccttgt gggcaaggat gatcctgatg    7920
actcatttct tctccatcct tctagctcag gaacaacttg aaaaagccct agattgtcag    7980
atctacgggg cctgttactc cattgagcca cttgacctac ctcagatcat tcaacgactc    8040
catggcctta gcgcattttc actccatagt tactctccag gtgagatcaa tagggtggct    8100
tcatgcctca ggaaacttgg ggtaccgccc ttgcgagtct ggagacatcg ggccagaagt    8160
gtccgcgcta ggctactgtc ccaggggggg agggctgcca cttgtggcaa gtacctcttc    8220
aactgggcag taaggaccaa gctcaaactc actccaatcc cggctgcgtc ccagttggat    8280
ttatccagct ggttcgttgc tggttacagc gggggagaca tatatcacag cctgtctcgt    8340
gcccgacccc gctggttcat gtggtgccta ctcctacttt ctgtaggggt aggcatctat    8400
ctactcccca accgatgaac ggggagctaa acactccagg ccaataggcc atcctgtttt    8460
tttccctttt tttttttctt ttttttttt ttttttttt ttttttttt ttctcctttt    8520
tttttcctct ttttttcctt ttctttcctt tggtggctcc atcttagccc tagtcacggc    8580
tagctgtgaa aggtccgtga gccgcttgac tgcagagagt gctgatactg gcctctctgc    8640
agatcaagt                                                            8649
```

<210> SEQ ID NO 5

<211> LENGTH: 8637
<212> TYPE: DNA
<213> ORGANISM: Hepatitis C virus

<400> SEQUENCE: 5
gccagccccc gattgggggc gacactccac catagatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcgagactgc tagccgagta gtgttgggtc gcgaaaggcc ttgtggtact gcctgatagg 300
gtgcttgcga gtgccccggg aggtctcgta gaccgtgcac catgagcacg aatcctaaac 360
ctcaaagaaa aaccaaaggg cgcgccatga ttgaacaaga tggattgcac gcaggttctc 420
cggccgcttg ggtggagagg ctattcggct atgactgggc acaacagaca atcggctgct 480
ctgatgccgc cgtgttccgg ctgtcagcgc aggggcgccc ggttcttttt gtcaagaccg 540
acctgtccgg tgccctgaat gaactgcagg acgaggcagc gcggctatcg tggctggcca 600
cgacgggcgt tccttgcgca gctgtgctcg acgttgtcac tgaagcggga agggactggc 660
tgctattggg cgaagtgccg gggcaggatc tcctgtcatc tcaccttgct cctgccgaga 720
aagtatccat catggctgat gcaatgcggc ggctgcatac gcttgatccg gctacctgcc 780
cattcgacca ccaagcgaaa catcgcatcg agcgagcacg tactcggatg gaagccggtc 840
ttgtcgatca ggatgatctg gacgaagagc atcaggggct cgcgccagcc gaactgttcg 900
ccaggctcaa ggcgcgcatg cccgacggcg aggatctcgt cgtgacccat ggcgatgcct 960
gcttgccgaa tatcatggtg gaaaatggcc gcttttctgg attcatcgac tgtggccggc 1020
tgggtgtggc ggaccgctat caggacatag cgttggctac ccgtgatatt gctgaagagc 1080
ttggcggcga atgggctgac cgcttcctcg tgctttacgg tatcgccgct cccgattcgc 1140
agcgcatcgc cttctatcgc cttcttgacg agttcttctg agtttaaaca gaccacaacg 1200
gtttccctct agcgggatca attccgcccc tctccctccc ccccccctaa cgttactggc 1260
cgaagccgct tggaataagg ccggtgtgcg tttgtctata tgttattttc caccatattg 1320
ccgtcttttg gcaatgtgag ggcccggaaa cctggccctg tcttcttgac gagcattcct 1380
aggggtcttt cccctctcgc caaaggaatg caaggtctgt tgaatgtcgt gaaggaagca 1440
gttcctctgg aagcttcttg aagacaaaca acgtctgtag cgaccctttg caggcagcgg 1500
aaccccccac ctggcgacag gtgcctctgc ggccaaaagc cacgtgtata agatacacct 1560
gcaaaggcgg cacaacccca gtgccacgtt gtgagttgga tagttgtgga aagagtcaaa 1620
tggctctcct caagcgtatt caacaagggg ctgaaggatg cccagaaggt accccattgt 1680
atgggatctg atctggggcc tcggtgcaca tgctttacat gtgtttagtc gaggttaaaa 1740
aacgtctagg ccccccgaac cacggggacg tggttttcct ttgaaaaaca cgataatacc 1800
atggaccggg agatggcagc atcgtgcgga ggcgcggttt tcgtaggtct gatactcttg 1860
accttgtcac cgcactataa gctgttcctc gctaggctca tatggtggtt acaatatttt 1920
atcaccaggg ccgaggcaca cttgcaagtg tggatccccc ccctcaacgt tcgggggggc 1980
cgcgatgccg tcatcctcct cacgtgcgcg atccacccag agctaatctt taccatcacc 2040
aaaatcttgc tcgccatact cggtccactc atggtgctcc aggctggtat aaccaaagtg 2100
ccgtacttcg tgcgcgcaca cgggctcatt cgtgcatgca tgctggtgcg gaaggttgct 2160
gggggtcatt atgtccaaat ggctctcatg aagttggccg cactgacagg tacgtacgtt 2220

-continued

```
tatgaccatc tcaccccact gcgggactgg gcccacgcgg gcctacgaga ccttgcggtg   2280
gcagttgagc ccgtcgtctt ctctgatatg gagaccaagg ttatcacctg gggggcagac   2340
accgcggcgt gtggggacat catcttgggc ctgcccgtct ccgcccgcag gggggaggag   2400
atacatctgg gaccggcaga cagccttgaa gggcaggggt ggcgactcct cgcgcctatt   2460
acggcctact cccaacagac gcgaggccta cttggctgca tcatcactag cctcacaggc   2520
cgggacagga accaggtcga gggggaggtc caagtggtct ccaccgcaac acaatctttc   2580
ctggcgacct gcgtcaatgg cgtgtgttgg actgtctatc atggtgccgg ctcaaagacc   2640
cttgccggcc caaagggccc aatcacccaa atgtacacca atgtggacca ggacctcgtc   2700
ggctggcaag cgcccccgg ggcgcgttcc ttgacaccat gcacctgcgg cagctcggac   2760
ctttacttgg tcacgaggca tgccgatgtc attccggtgc gccggcgggg cgacagcagg   2820
gggagcctac tctcccccag gcccgtctcc tacttgaagg gctcttcggg cggtccactg   2880
ctctgcccct cggggcacgc tgtgggcatc tttcgggctg ccgtgtgcac ccgaggggtt   2940
gcgaaggcgg tggactttgt acccgtcgag tctatggaaa ccactatgcg gtccccggtc   3000
ttcacggaca actcgtcccc tccggccgta ccgcagacat tccaggtggc ccatctacac   3060
gcccctactg gtagcggcaa gagcactaag gtgccggctg cgtatgcagc ccaagggtat   3120
aaggtgcttg tcctgaaccc gtccgtcgcc gccaccctag gtttcggggc gtatatgtct   3180
aaggcacatg gtatcgaccc taacatcaga accggggtaa ggaccatcac cacgggtgcc   3240
cccatcacgt actccaccta tggcaagttt cttgccgacg gtggttgctc tgggggcgcc   3300
tatgacatca taatatgtga tgagtgccac tcaactgact cgaccactat cctgggcatc   3360
ggcacagtcc tggaccaagc ggagacggct ggagcgcgac tcgtcgtgct cgccaccgct   3420
acgcctccgg gatcggtcac cgtgccacat ccaaacatcg aggaggtggc tctgtccagc   3480
actggagaaa tcccctttta tggcaaagcc atccccatcg agaccatcaa ggggggggagg   3540
cacctcattt tctgccattc caagaagaaa tgtgatgagc tcgccgcgaa gctgtccggc   3600
ctcggactca atgctgtagc atattaccgg ggccttgatg tatccgtcat accaactagc   3660
ggagacgtca ttgtcgtagc aacggacgct ctaatgacgg gctttaccgg cgatttcgac   3720
tcagtgatcg actgcaatac atgtgtcacc cagacagtcg acttcagcct ggacccgacc   3780
ttcaccattg agacgacgac cgtgccacaa gacgcggtgt cacgctcgca gcggcgaggc   3840
aggactggta ggggcaggat gggcatttac aggtttgtga ctccaggaga acggccctcg   3900
ggcatgttcg attcctcggt tctgtgcgag tgctatgacg cgggctgtgc ttggtacgag   3960
ctcacgcccg ccgagacctc agttaggttg cgggcttacc taaacacacc agggttgccc   4020
gtctgccagg accatctgga gttctgggag agcgtcttta caggcctcac ccacatagac   4080
gcccatttct tgtcccagac taagcaggca ggagacaact tcccctacct ggtagcatac   4140
caggctacgg tgtgcgccag ggctcaggct ccacctccat cgtgggacca aatgtggaag   4200
tgtctcatac ggctaaagcc tacgctgcac gggccaacgc ccctgctgta taggctggga   4260
gccgttcaaa acgaggttac taccacacac cccataacca aatacatcat ggcatgcatg   4320
tcggctgacc tggaggtcgt cacgagcacc tgggtgctgg taggcggagt cctagcagct   4380
ctggccgcgt attgcctgac aacaggcagc gtggtcattg tgggcaggat catcttgtcc   4440
ggaaagccgg ccatcattcc cgacagggaa gtcctttacc gggagttcga tgagatggaa   4500
gagtgcgcct cacacctccc ttacatcgaa cagggaatgc agctcgccga acaattcaaa   4560
cagaaggcaa tcgggttgct gcaaacagcc accaagcaag cggaggctgc tgctcccgtg   4620
```

-continued

```
gtggaatcca agtggcggac cctcgaagcc ttctgggcga agcatatgtg gaatttcatc   4680
agcgggatac aatatttagc aggcttgtcc actctgcctg gcaaccccgc gatagcatca   4740
ctgatggcat tcacagcctc tatcaccagc ccgctcacca cccaacatac cctcctgttt   4800
aacatcctgg ggggatgggt ggccgcccaa cttgctcctc ccagcgctgc ttctgctttc   4860
gtaggcgccg gcatcgctgg agcggctgtt ggcagcatag gccttgggaa ggtgcttgtg   4920
gatattttgg caggttatgg agcaggggtg gcaggcgcgc tcgtggcctt taaggtcatg   4980
agcggcgaga tgccctccac cgaggacctg gttaacctac tccctgctat cctctcccct   5040
ggcgccctag tcgtcggggt cgtgtgcgca gcgatactgc gtcggcacgt gggcccaggg   5100
gagggggctg tgcagtggat gaaccggctg atagcgttcg cttcgcgggg taaccacgtc   5160
tcccccacgc actatgtgcc tgagagcgac gctgcagcac gtgtcactca gatcctctct   5220
agtcttacca tcactcagct gctgaagagg cttcaccagt ggatcaacga ggactgctcc   5280
acgccatgct ccggctcgtg gctaagagat gtttgggatt ggatatgcac ggtgttgact   5340
gatttcaaga cctggctcca gtccaagctc ctgccgcgat tgccgggagt ccccttcttc   5400
tcatgtcaac gtgggtacaa gggagtctgg cggggcgacg gcatcatgca aaccacctgc   5460
ccatgtggag cacagatcac cggacatgtg aaaaacggtt ccatgaggat cgtggggcct   5520
aggacctgta gtaacacgtg gcatggaaca ttccccatta acgcgtacac cacgggcccc   5580
tgcacgccct ccccggcgcc aaattattct agggcgctgt ggcgggtggc tgctgaggag   5640
tacgtggagg ttacgcgggt gggggatttc cactacgtga cgggcatgac cactgacaac   5700
gtaaagtgcc cgtgtcaggt tccggccccc gaattcttca cagaagtgga tggggtgcgg   5760
ttgcacaggt acgctccagc gtgcaaaccc ctcctacggg aggaggtcac attcctggtc   5820
gggctcaatc aatacctggt tgggtcacag ctcccatgcg agcccgaacc ggacgtagca   5880
gtgctcactt ccatgctcac cgacccctcc cacattacgg cggagacggc taagcgtagg   5940
ctggccaggg gatctccccc ctccttggcc agctcatcag ctagccagct gtctgcgcct   6000
tccttgaagg caacatgcac tacccgtcat gactccccgg acgctgacct catcgaggcc   6060
aacctcctgt ggcggcagga gatgggcggg aacatcaccc gcgtggagtc agaaaataag   6120
gtagtaattt tggactcttt cgagccgctc caagcggagg aggatgagag ggaagtatcc   6180
gttccggcgg agatcctgcg gaggtccagg aaattccctc gagcgatgcc catatgggca   6240
cgcccggatt acaaccctcc actgttagag tcctggaagg acccggacta cgtccctcca   6300
gtggtacacg ggtgtccatt gccgcctgcc aaggcccctc cgataccacc tccacggagg   6360
aagaggacgg ttgtcctgtc agaatctacc gtgtcttctg ccttggcgga gctcgccaca   6420
aagaccttcg gcagctccga atcgtcggcc gtcgacagcg gcacggcaac ggcctctcct   6480
gaccagccct ccgacgacgg cgacgcggga tccgacgttg agtcgtactc ctccatgccc   6540
ccccttgagg gggagccggg ggatcccgat ctcagcgacg ggtcttggtc taccgtaagc   6600
gaggaggcta gtgaggacgt cgtctgctgc tcgatgtcct acacatggac aggcgccctg   6660
atcacgccat gcgctgcgga ggaaaccaag ctgcccatca atgcactgag caactctttg   6720
ctccgtcacc acaacttggt ctatgctaca acatctcgca gcgcaagcct gcggcagaag   6780
aaggtcacct ttgacagact gcaggtcctg gacgaccact accgggacgt gctcaaggag   6840
atgaaggcga aggcgtccac agttaaggct aaacttctat ccgtggagga agcctgtaag   6900
ctgacgcccc cacattcggc cagatctaaa tttggctatg ggcaaaggga cgtccggaac   6960
ctatccagca aggccgttaa ccacatccgc tccgtgtgga aggacttgct ggaagacact   7020
```

-continued

```
gagacaccaa ttgacaccac catcatggca aaaaatgagg ttttctgcgt ccaaccagag   7080
aaggggggcc gcaagccagc tcgccttatc gtattcccag atttgggggt tcgtgtgtgc   7140
gagaaaatgg ccctttacga tgtggtctcc accctccctc aggccgtgat gggctcttca   7200
tacggattcc aatactctcc tggacagcgg gtcgagttcc tggtgaatgc ctggaaagcg   7260
aagaaatgcc ctatgggctt cgcatatgac acccgctgtt ttgactcaac ggtcactgag   7320
aatgacatcc gtgttgagga gtcaatctac caatgttgtg acttggcccc cgaagccaga   7380
caggccataa ggtcgctcac agagcggctt tacatcgggg gcccccctgac taattctaaa   7440
gggcagaact gcggctatcg ccggtgccgc gcgagcggtg tactgacgac cagctgcggt   7500
aataccctca catgttactt gaaggccgct gcggcctgtc gagctgcgaa gctccaggac   7560
tgcacgatgc tcgtatgcgg agacgacctt gtcgttatct gtgaaagcgc ggggacccaa   7620
gaggacgagg cgagcctacg ggccttcacg gaggctatga ctagatactc tgccccccct   7680
ggggacccgc ccaaaccaga atacgacttg gagttgataa catcatgctc ctccaatgtg   7740
tcagtcgcgc acgatgcatc tggcaaaagg gtgtactatc tcacccgtga ccccaccacc   7800
ccccttgcgc gggctgcgtg ggagacagct agacacactc cagtcaattc ctggctaggc   7860
aacatcatca tgtatgcgcc caccttgtgg gcaaggatga tcctgatgac tcatttcttc   7920
tccatccttc tagctcagga acaacttgaa aaagccctag attgtcagat ctacggggcc   7980
tgttactcca ttgagccact tgacctacct cagatcattc aacgactcca tggccttagc   8040
gcattttcac tccatagtta ctctccaggt gagatcaata gggtggcttc atgcctcagg   8100
aaacttgggg taccgccctt gcgagtctgg agacatcggg ccagaagtgt ccgcgctagg   8160
ctactgtccc aggggggggag ggctgccact tgtggcaagt acctcttcaa ctgggcagta   8220
aggaccaagc tcaaactcac tccaatcccg gctgcgtccc agttggattt atccagctgg   8280
ttcgttgctg gttacagcgg gggagacata tatcacagcc tgtctcgtgc ccgaccccgc   8340
tggttcatgt ggtgcctact cctactttct gtaggggtag gcatctatct actccccaac   8400
cgatgaacgg ggagctaaac actccaggcc aataggccat cctgtttttt tccctttttt   8460
tttttctttt tttttttttt tttttttttt tttttttttt ctcctttttt tttcctcttt   8520
ttttcctttt ctttcctttg gtggctccat cttagcccta gtcacggcta gctgtgaaag   8580
gtccgtgagc cgcttgactg cagagagtgc tgatactggc ctctctgcag atcaagt      8637
```

<210> SEQ ID NO 6
<211> LENGTH: 419
<212> TYPE: DNA
<213> ORGANISM: Hepatitis C virus

<400> SEQUENCE: 6

```
gggggcgaca ctccaccata gatcactccc ctgtgaggaa ctactgtctt cacgcagaaa     60
gcgtctagcc atggcgttag tatgagtgtc gtgcagcctc caggaccccc cctcccggga    120
gagccatagt ggtctgcgga accggtgagt acaccggaat tgccaggacg accgggtcct    180
ttcttggatc aacccgctca atgcctggag atttgggcgt gcccccgcga gactgctagc    240
cgagtagtgt tgggtcgcga aaggccttgt ggtactgcct gatagggtgc ttgcgagtgc    300
cccgggaggt ctcgtagacc gtgcaccatg agcacgaatc ctaaacctca aagaaaaacc    360
aaagggcgcg ccatgattga acaagatgga ttgcacgcag gttctccggc cgcttgggt     419
```

<210> SEQ ID NO 7
<211> LENGTH: 23
<212> TYPE: DNA

-continued

```
<213> ORGANISM: Artificial
<220> FEATURE:
<223> OTHER INFORMATION: Primer sequence

<400> SEQUENCE: 7

gggggcgaca ctccaccata gat                                              23


<210> SEQ ID NO 8
<211> LENGTH: 41
<212> TYPE: DNA
<213> ORGANISM: Artificial
<220> FEATURE:
<223> OTHER INFORMATION: Primer sequence

<400> SEQUENCE: 8

atttaggtga cactatagaa acccaagcgg ccggagaacc t                          41
```

QUANTITATIVE ASSAY FOR DETECTION OF NEWLY SYNTHESIZED RNA IN A CELL-FREE SYSTEM AND IDENTIFICATION OF RNA SYNTHESIS INHIBITORS

CROSS-REFERENCE TO RELATED APPLICATION

This application claims priority from U.S. provisional application 60/555,765 filed Mar. 24, 2004, which is hereby incorporated in its entirety.

BACKGROUND

HCV is one of the most prevalent causes of chronic liver disease in the United States, which accounts for about 15 percent of acute viral hepatitis, 60 to 70 percent of chronic hepatitis, and up to 50 percent of cirrhosis, end-stage liver disease, and liver cancer. Almost 4 million Americans, or 1.8 percent of the U.S. population, have antibodies to HCV (i.e., anti-HCV antibodies), indicating ongoing or previous infection with the virus. Hepatitis C causes an estimated 8,000 to 10,000 deaths annually in the United States. While the acute phase of HCV infection is usually associated with mild symptoms, some evidence suggests that only about 15% to about 20% of the infected people will clear HCV.

HCV is a small, enveloped, single-stranded positive strand RNA virus in the Flaviviridae family. The genome includes approximately 10,000 nucleotides and encodes a single polyprotein of about 3,000 amino acids. All of the protein products of HCV are produced by proteolytic cleavage of the polyprotein, carried out by one of three proteases: the host signal peptidase, the viral self-cleaving metalloproteinase (NS2), and the viral serine protease (NS3/4A). The combined action of these enzymes produces the structural proteins (C, E1 and E2) and non-structural proteins (NS2, NS3, NS4A, NS4B, NS5A, and NS5B) that are required for replication and packaging of the viral genomic RNA. NS5B is the viral RNA-dependent RNA polymerase (RDRP) that is responsible for the conversion of the input genomic RNA into a minus strand copy (complimentary RNA, or cRNA); the cRNA then serves as a template for transcription by NS5B of the positive sense genomic/messenger RNA. The HCV replicase is the complex of proteins that are necessary for the accurate and efficient synthesis of viral replicon RNA.

Currently, the only effective therapy against HCV is alpha-interferon, which reduces the amount of virus in the liver and blood (e.g., viral load) in only a small proportion of infected patients. Standard forms of interferon, however, are now being replaced by pegylated interferons (peginterferons), alpha interferons that have been modified chemically by the addition of a large inert molecule of polyethylene glycol. At the present time, the optimal regimen including interferon appears to be a 24- or 48-week course of a combination of pegylated alpha interferon and the nucleoside ribavirin, an oral antiviral agent that has activity against a broad range of viruses. Nonetheless, response rates to the combination interferon/ribavirin therapy may be moderate for certain HCV genotypes, i.e., a response rate of about 50% to about 60%, although response rates for selected genotypes of HCV (notably genotypes 2 and 3) are typically higher. Another drawback to the current therapy is that there are often significant adverse side effects associated with each of these agents including, for example, flu-like symptoms; bone marrow suppressive effects; neuropsychiatric effects such as marked irritability, anxiety, personality changes, depression, and even suicide or acute psychosis; histamine-like side effects; and anemia.

Taken together, the preceding facts indicate a significant need for effective small molecule inhibitors of HCV replication that do not suffer from the above-mentioned drawbacks. A particularly useful class of inhibitors of HCV, as well as other positive strand RNA viruses, is inhibitors of viral RNA synthesis.

While accurate and efficient assays for identifying HCV RNA synthesis inhibitors may be useful tools for identifying effective small molecule HCV therapeutics, no such system has been developed. An in vitro replication assay using recombinant NS5B polymerase has been reported. However, in this system, the purified form of NS5B polymerase lacked template specificity and produced various lengths of RNA products. These phenomena are very different from HCV RNA replication in vivo. To better reflect the HCV RNA replication process in the cell, a cell-free HCV replication system was established using whole cell lysates or membrane fractions of cells expressing the HCV replicon. In this cell-free system, radioactive $P^{32}$-UTP or $P^{32}$-CTP was used to label newly synthesized HCV RNA, and then the reaction products were resolved by gel electrophoresis, followed by autoradiography. Because these assays require gel electrophoresis to separate the full length HCV RNA from other RNA molecules, the results are difficult to quantify, often inaccurate, and poorly reproducible. Additionally, while it appears to be clear that RNA elongation occurs in this cell-free system, there is no convincing evidence that de novo RNA initiation occurs in this system.

SUMMARY

An assay for detecting newly synthesized viral RNA in a cell-free system, and for identifying compounds that inhibit positive strand RNA viruses such as the Hepatitis C Virus (HCV) is provided herein.

Provided herein is an assay for detecting newly synthesized RNA from a positive strand RNA virus, such as HCV virus, which is more efficient and quantitative than previously reported assays. This assay is useful for identifying inhibitors of RNA synthesis of a positive strand RNA virus, including inhibitors of HCV RNA synthesis. Certain embodiments of the assay include methods for distinguishing RNA synthesis initiation inhibitors from RNA elongation inhibitors.

Provided herein is a method for determining whether a test compound inhibits RNA synthesis of a positive strand RNA virus. The method comprises:

contacting an isolated replicase complex for the positive strand RNA virus, an isolated viral replicon template RNA for the positive strand RNA virus, a labeled nucleotide analog, and the test compound, under conditions sufficient for in vitro RNA synthesis, to form a newly synthesized RNA population comprising the labeled nucleotide analog;

detecting the newly synthesized RNA population comprising the labeled nucleotide analog;

quantitating the newly synthesized RNA population comprising the labeled nucleotide analog to provide a test RNA amount; and comparing the test RNA amount with a control RNA amount of a control newly synthesized RNA population comprising the labeled nucleotide analog produced in the absence of the test compound, wherein a decrease in the test RNA amount compared to the control RNA amount indicates that the test compound inhibits RNA synthesis of the positive strand RNA virus.

Further provided herein is a method for quantitating newly initiated RNA of a positive strand RNA virus comprising:

contacting an isolated replicase complex for the positive strand RNA virus, an isolated viral replicon template RNA for the positive strand RNA virus, and a labeled nucleotide analog, under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of a transcription initiation region of the newly synthesized RNA population;

digesting unhybridized, single-stranded RNA with a single-strand specific ribonuclease to form a protected RNA population comprising the labeled nucleotide analog;

detecting the protected RNA population comprising the labeled nucleotide analog; and quantitating the protected RNA population comprising the labeled nucleotide analog.

Also provided is a method for determining whether a test compound is an RNA synthesis initiation inhibitor of a positive strand RNA virus comprising:

contacting an isolated replicase complex for the positive strand RNA virus, an isolated viral replicon template RNA for the positive strand RNA virus, a labeled nucleotide analog, and the test compound, under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of an initiation region of the newly synthesized RNA population;

digesting unhybridized, single-stranded RNA with a single-strand specific ribonuclease to form a protected RNA population;

detecting a protected RNA population comprising the labeled nucleotide analog;

quantitating the protected RNA population comprising the labeled nucleotide analog to provide a test RNA amount; and comparing the test RNA amount with a control RNA amount of protected RNA comprising the labeled nucleotide analog but produced in the absence of the test compound, wherein a decrease in the test RNA amount compared to the control RNA amount indicates that the test compound inhibits RNA synthesis initiation of the positive strand RNA virus.

DETAILED DESCRIPTION

Figure 1:
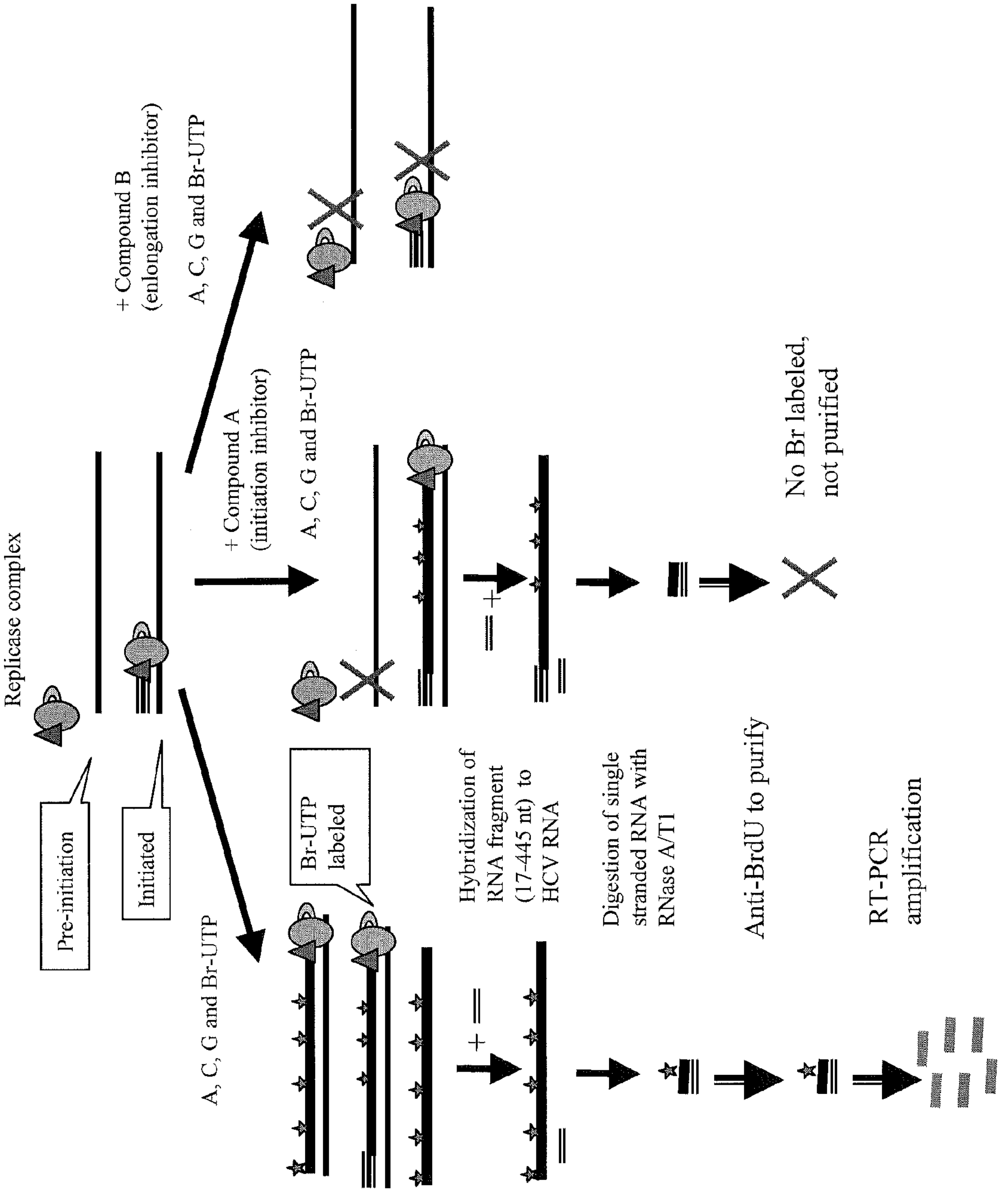
FIG. 1 shows a schematic of the inhibition of HCV replicon replication by transcription initiation and elongation inhibitors.

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

Terminology and Molecular Description

A "replicon" as used herein includes a genetic element, for example, a plasmid, cosmid, bacmid, phage or virus that is capable of replication largely under its own control. A "replicon RNA" includes RNA produced by transcription of a replicon, e.g., a double-stranded DNA replicon. A replicon may be either RNA or DNA, and may be single or double-stranded. A suitable replicon is a replicon from a single-stranded positive strand RNA virus such as a virus of the Picornaviridae family, the Calciviride family, the Togaviridae family, the Coronaviridae family, or the Flaviviridae family. Viruses of the Flaviviridae family include, for example, Hepatitis C Virus, West Nile Virus, Dengue Virus, Kunjuin Virus, Yellow Fever Virus, Bovine Viral Diarrhea Virus, Tick Born Encephalitis Virus, Japanese Encephalitis Virus, and Venezuelan Equine Encephalitis Virus. In one embodiment, the replicon is a Hepatitis C Virus replicon.

In positive strand RNA viruses, replication is performed by a multi-protein-RNA complex called a "replicase complex". As used herein, a "replicase complex" is an active complex of polypeptides and RNA which is capable of complete and accurate viral replicon RNA synthesis under cell-free conditions suitable for viral RNA replication. By complete and accurate viral replicon RNA synthesis, it is meant that the replicase complex is capable of producing full-length viral replicon RNAs. In addition, the isolated replicase complex should show specificity for replication of the replicase RNA of the corresponding positive strand RNA virus. In one embodiment, an isolated replicase complex comprises a viral replicon template RNA for the positive strand RNA virus. An "isolated replicase complex" is a replicase complex which has been removed from its natural cellular environment, such as a cell expressing a viral replicon RNA. "Isolated replicase complex" includes the membrane fraction of a cell expressing the viral replicase RNA. The isolated replicase complex may be separated from the cell nucleus, chromosomal DNA, and cytoplasmic materials, for example. In addition, an isolated replicase complex may comprise one or more polypeptides expressed from a recombinant expression system, so long as the complex is capable of complete and accurate viral replicon RNA synthesis. The replicase complex of HCV, for example, includes the NS5B protein which has RNA-dependent RNA polymerase activity, and other protein factors "Nucleic acid" or a "nucleic acid molecule" refers to a DNA or RNA molecule, either single or double-stranded and, if single-stranded, the molecule of its complementary sequence in either linear or circular form. A sequence or structure of a particular nucleic acid molecule can be described according to the normal convention of providing the sequence in the 5' to 3' direction.

The term "isolated nucleic acid molecule" includes nucleic acid molecules that are separated from an intact cellular environment. An "isolated nucleic acid molecule" may be, for example, a template RNA that is separated from the cell nucleus, chromosomal DNA, and other cellular materials which are not membrane-associated. Moreover, an "isolated" nucleic acid molecule, such as a viral replicon template RNA molecule, can be substantially free of other cellular material, or culture medium when produced by recombinant techniques, or substantially free of chemical precursors or other chemicals when chemically synthesized. In some embodiments, an isolated viral replicon template RNA may be purified as a portion of a membrane fraction of a cell expressing a viral replicon RNA. Such a membrane fraction may also comprise isolated replicase complexes. Substantially free of other cellular material includes, for example, a cellular fraction such as, for example, a membrane bound fraction. By substantially free of other cellular material, it is meant that an isolated nucleic acid molecule may be greater than or equal to about 70%, about 75%, about 80%, about 85%, about 90%, about 95% or about 99% free of unwanted cellular materials, such as, for example, components of cellular fractions other than the membrane-bound fraction.

In some embodiments, an "isolated" nucleic acid may be free of sequences which naturally flank the nucleic acid (i.e., sequences located at the 5' and/or 3' ends of the nucleic acid) in the genomic DNA or RNA of the organism from which the nucleic acid is derived. For example, the isolated nucleic acid molecule may contain less than about 5 kb, about 4 kb, about 3 kb, about 2 kb, about 1 kb, about 0.5 kb or about 0.1 kb of 5' and/or 3' nucleotide sequences which naturally flank the nucleic acid molecule in genomic DNA of the cell from which the nucleic acid is derived. In this sense, an isolated nucleic acid may be, for example, a DNA vector encoding a viral replicon RNA which has been purified by standard DNA purification methods.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that greater than or equal to about 75%, but often, greater than or equal to about 90%, of the nucleotides of the sequence match over the defined length of the nucleic acid sequence. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

Different "variants" including "natural allelic variants" of, for example, the HCV genome exist in nature. These variants may be alleles characterized by differences in the nucleotide sequences of the gene coding for a protein, or may involve different RNA processing or post-translational modifications. The skilled person can produce variants having single or multiple amino acid substitutions, deletions, additions or replacements. These variants may include inter alia: a) variants in which one or more amino acids residues are substituted with conservative or non-conservative amino acids, b) variants in which one or more amino acids are added, and c) variants in which one or more amino acids include a substituent group.

"Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., atg) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included. A replicon may include operably linked expression control sequences.

The term "probe" as used herein refers to an oligonucleotide or polynucleotide comprising either RNA or DNA, whether occurring naturally as in a purified restriction enzyme digest or produced synthetically, which is capable of annealing with or specifically hybridizing to a nucleic acid with sequences complementary to the probe. A probe may be, for example, a single-stranded RNA transcribed in vitro from a DNA template. A probe may be either single-stranded or double-stranded, and in one embodiment is single-stranded. The exact length of the probe will depend upon many factors, including the temperature, the source of the probe, and use. The probes are selected to be "substantially" complementary to a strand of a particular target nucleic acid sequence. This means that the probes are sufficiently complementary so as to be able to "specifically hybridize" or anneal with their respective target strands under a set of pre-determined conditions. The term specifically hybridize means that the probe has a greater probability of hybridizing to its target sequence than other non-target sequences.

Therefore, the probe sequence need not reflect the exact complementary sequence of the target. For example, a non-complementary nucleotide fragment may be attached to the 5' or 3' end of the probe, with the remainder of the probe sequence being complementary to the target strand. A small (e.g., less than or equal to about 10%) of mismatched nucleotides in the primer and the target sequence is also permissible.

The term "oligonucleotide" is defined as a nucleic acid molecule comprising two or more ribonucleotides or deoxyribonucleotides, preferably more than three. The exact size of the oligonucleotide will depend on various factors and on the particular application and use of the oligonucleotide. In one embodiment, an oligonucleotide comprises less than 100 nucleotides, more specifically less than or equal to about 50 nucleotides, and most specifically less than or equal to about 30 nucleotides.

A "polynucleotide" probe or primer specifically comprises less than or equal to about 1000 nucleotides, more specifically less than or equal to about 800 nucleotides, and most specifically less than or equal to about 500 nucleotides. A polynucleotide primer also specifically comprises greater than or equal to about 100 nucleotides, more specifically greater than or equal to about 150 nucleotides, and most specifically greater than or equal to about 200 nucleotides.

"Stringency conditions" for hybridization is a term of art which refers to the incubation and wash conditions, e.g., conditions of temperature and buffer concentration, which permit hybridization of a first nucleic acid to a second nucleic acid; the first nucleic acid may be perfectly (i.e., 100%)

complementary to the second, or the first and second may share some degree of complementarity which is less than perfect (e.g., 70%, 75%, 85%, 95%, 98%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained in *Current Protocols in Molecular Biology* (Ausubel, F. M. et al., "*Current Protocols in Molecular Biology*", John Wiley & Sons, (1998)). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. SSC buffer is 150 mM sodium chloride and 15 mM sodium citrate, pH 7.0. High, moderate or low stringency conditions can be determined empirically.

By varying stringency conditions for hybridization from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology,* 200:546-556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Starting from the lowest temperature at which only homologous hybridization occurs, each ° C. by which the final wash temperature is reduced (holding SSC concentration constant) allows an increase by about 1% in the maximum extent of mismatching among the sequences that hybridize. Generally, doubling the concentration of SSC results in an increase in $T_m$ of about 17° C. Using these guidelines, the washing temperature can be determined empirically for high, moderate or low stringency, depending on the level of mismatch sought.

For example, a low stringency wash can comprise washing in a solution containing 0.2×SSC/0.1% sodium dodecyl sulfate (SDS) for 10 minutes at room temperature; a moderate stringency wash can comprise washing in a prewarmed solution (42° C.) solution containing 0.2×SSC/0.1% SDS for 15 minutes at 42° C.; and a high stringency wash can comprise washing in prewarmed (68° C.) solution containing 0.1×SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

A "test compound" as defined herein refers to a chemical, nucleic acid, polypeptide, amino acid, or other compound which is to be tested. Examples of test compounds include, but are not limited to, drug candidates, such as derived from arrays of small molecules generated through general combinatorial chemistry, as well as any other substances thought to have potential biological activity.

DESCRIPTION OF THE ASSAYS

Provided herein is a method for determining whether a test compound inhibits RNA synthesis of a positive strand RNA virus. The method comprises:

contacting an isolated replicase complex for the positive strand RNA virus, an isolated viral replicon template RNA for the positive strand RNA virus, a labeled nucleotide analog, and the test compound, under conditions sufficient for in vitro RNA synthesis, to form a newly synthesized RNA population comprising the labeled nucleotide analog;

detecting the newly synthesized RNA population comprising the labeled nucleotide analog;

quantitating the newly synthesized RNA population comprising the labeled nucleotide analog to provide a test RNA amount; and comparing the test RNA amount with a control RNA amount of a control newly synthesized RNA population comprising the labeled nucleotide analog produced in the absence of the test compound, wherein a decrease in the test RNA amount compared to the control RNA amount indicates that the test compound inhibits RNA synthesis of the positive strand RNA virus.

Further provided herein is a method for quantitating newly initiated RNA of a positive strand RNA virus comprising:

contacting an isolated replicase complex for the positive strand RNA virus, an isolated viral replicon template RNA for the positive strand RNA virus, and a labeled nucleotide analog, under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of a transcription initiation region of the newly synthesized RNA population;

digesting unhybridized, single-stranded RNA with a single-strand specific ribonuclease to form a protected RNA population comprising the labeled nucleotide analog;

detecting the protected RNA population comprising the labeled nucleotide analog; and quantitating the protected RNA population comprising the labeled nucleotide analog.

Also provided is a method for determining whether a test compound is an RNA synthesis initiation inhibitor of a positive strand RNA virus comprising:

contacting an isolated replicase complex for the positive strand RNA virus, an isolated viral replicon template RNA for the positive strand RNA virus, a labeled nucleotide analog, and the test compound, under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of an initiation region of the newly synthesized RNA population;

digesting unhybridized, single-stranded RNA with a single-strand specific ribonuclease to form a protected RNA population;

detecting a protected RNA population comprising the labeled nucleotide analog;

quantitating the protected RNA population comprising the labeled nucleotide analog to provide a test RNA amount; and comparing the test RNA amount with a control RNA amount of protected RNA comprising the labeled nucleotide analog but produced in the absence of the test compound, wherein a decrease in the test RNA amount compared to the control RNA amount indicates that the test compound inhibits RNA synthesis initiation of the positive strand RNA virus.

In some embodiments of the above methods, the isolated viral replicase complexes and the isolated viral replicon template RNA are provided by transfecting a cell line with an isolated DNA template for a viral replicon or an isolated viral RNA, to provide a transfected cell line, incubating the transfected cell line under conditions suitable for viral replication, and isolating replicase complexes and viral replicon template RNA from the cell membrane fraction of the transfected cell line.

In other embodiments of the above methods, the isolated viral replicase complexes and isolated viral replicon template RNAs may be provided by acutely infected or persistent infected primary hepatocytes, lymphocytes or other cell lines, incubating the infected cell line under conditions suitable for viral replication, and isolating the replicase complexes comprising viral replicon RNA from the cell membrane fraction. The replicase complexes may be isolated from infected primary cells or cell lines.

In certain embodiments of the methods described herein, the positive strand RNA virus is Hepatitis C Virus, and a suitable DNA template for the HCV viral replicon is, for example, SEQ ID NO: 1, which can also be described as GeiBank Accession No. AJ242652. Other suitable replicon template DNAs include, for example, AB114136, AJ242654, AJ242653, and AJ242651 (SEQ ID NOs. 2-5).

In certain embodiments of the methods, the labeled nucleotide analog is an analog capable of being recognized by a specific antibody, an analog which can be recognized via a high specificity binding reaction, or an analog directly detectable as a result of a physical property of the analog. In some embodiments, the labeled nucleotide analog is an analog capable of being recognized by a specific antibody, such as 5'-bromouridine 5'-triphosphate (Br-UTP). In other embodiments, the labeled nucleotide analog is a radioactively labeled nucleotide.

In the methods described herein, detection of a newly synthesized RNA population may be accomplished by contacting a newly synthesized RNA population with an antibody specific for the labeled nucleotide analog, and immuno-precipitating the newly synthesized RNA population comprising the labeled nucleotide analog to form an immuno-precipitated RNA population. In some embodiments, the nucleotide analog is Br-UTP, and the specific antibody is an anti-BrdU antibody. The methods described herein include quantitating the newly synthesized RNA population by performing real time PCR on the immuno-precipitated RNA population. In other embodiments, detection of a newly synthesized RNA population may be accomplished by detecting a radioactively labeled nucleotide by, for example, non-denaturing gel electrophoresis followed by autoradiography.

In some embodiments, a 2'-O-methylated nucleotide may be employed during the replication reaction to increase the yield of newly synthesized RNA.

In order to form a newly synthesized RNA population, an isolated replicase complex and isolated viral replicase RNA template are employed. The isolated viral replicon template RNA comprises a transcription initiation region. The template RNA may be, for example, isolated as a component of the replicase complex. In some embodiments, an isolated viral template RNA may be added to the replicase complex.

A viral replicon RNA or DNA vector encoding the viral replicon RNA may be transfected into a cell line suitable for expression of the viral replicon RNA. Suitable cell lines include, for example, mammalian cell lines such as Vero cells, HeLa cells, CHO cells, COS cells, WI38 cells, N1H-3T3 cells (and other fibroblast cells, such as MRC-5 cells), MDCK cells, KB cells, SW-13 cells, MCF7 cells, BHK cells, HEK-293 cells, HepG2 cells, Bowes melanoma cells cell lines; and chicken embryonic fibroblast (CEF) cell lines. In one embodiment, the cell line is a human cell line, such as, for example, a human hepatosoma cell line such as Huh-7. Suitable means of transfection include, for example, calcium phosphate co-precipitates, mechanical procedures such as microinjection, electroporation, insertion of a plasmid encased in liposomes, as well as other techniques known in the art.

A suitable DNA vector for production of an HCV replicon RNA, for example, comprises, 5'-3', the HCV-IRES, the neomycin phosphotransferase (neo) gene, the IRES of encephalomyocarditis virus, which directs translation of HCV sequences NS3 to NS5B, and the 3'-NTR. The sequence of a DNA vector suitable for production of the HCV replicon RNA has been deposited in GenBank (Accession no. AJ242652) (SEQ ID NO:1). The HCV replicon DNA vector may be transfected into Huh-7 cells by electroporation. HCV replicon RNA may be transcribed in vitro using either SP6 RNA polymerase or T7 RNA polymerase, for example, from a plasmid DNA comprising the appropriate promoter with the cDNA encoding the replicon RNA downstream of the promoter. The DNA template for production of a viral replicase RNA may be produced by PCR amplification using a DNA template encoding the viral replicon and specific primers one of which comprises an SP6 or T7 RNA polymerase promoter. Alternatively, the DNA template for production of a viral replicase RNA may be produced by reverse transcription of the viral replicase RNA using primers one of which comprises an SP6 or T7 RNA polymerase promoter.

Once the viral replicon RNA or DNA vector encoding the viral replicon RNA is transfected into a cell, the cell culture may be grown to confluency. The cells in the culture produce replicase complexes comprising viral replicon template RNAs, which can then be isolated from the cells. Viral replicon RNA includes minus strand viral replicon template RNA, and optionally positive strand RNA.

Alternatively, infected cells such as acutely infected or persistent infected primary hepatocytes, lymphocytes or other cell lines may be employed to isolated viral replicon RNA. Infected primary cells or cell lines may be employed. The infected cell line is incubated under conditions suitable for viral replication, and the replicase complexes comprising viral replicon RNA are isolated from the cell membrane fraction.

In order to isolate replication complexes and viral replicon template RNA, the cells (i.e., transfected or infected with a viral replicon) may be lysed and centrifuged at low speed (e.g., about 900×to about 1000×g) to remove cellular debris. The supernatant may then be centrifuged at higher speed (e.g., about 15000×g) to obtain the membrane fraction, which comprises isolated viral replicon complexes and optionally comprises viral replicon template RNA. It has been shown that replication of the HCV RNA occurs in a membrane-bound replication complex. Thus, HCV replicon complexes and replicon template RNA can be isolated by isolating the membrane fraction of the cells expressing the HCV replicon RNA.

The isolated membrane fraction containing replicase complexes (e.g., an aliquot of the membrane fraction of a cell line expressing a viral RNA replicon) and isolated replicon template RNA are used to perform RNA replication in vitro in a cell-free system. The isolated replicase complexes and isolated viral replicon template RNA are contacted with a labeled nucleotide analog under conditions sufficient to promote in vitro RNA synthesis. Conditions sufficient to promote in vitro RNA synthesis include suitable buffers, and nucleoside triphosphates (i.e., ATP, UTP, CTP, and GTP). The labeled nucleotide analog is incorporated into a newly synthesized RNA population, and provides a means for detecting only the newly synthesized RNA, and not the template RNA. In one embodiment, suitable conditions for replication include, for example, incubation in 50 μl (total volume) of 50 mM HEPES (pH 7.5), 10 mM KCl, 10 mM $MgCl_2$, 50 units RNasin, 10 μg/ml actinomycin D, 2.5 mM ATP, 0.5 mM each CTP, GTP, labeled UTP and an aliquot of a membrane fraction of a cell line expressing the viral replicon RNA, e.g., isolated replicase complexes and isolated viral replicon template RNA. In another embodiment, suitable replication conditions include 50 mM HEPES (pH 7.3); 10 mM KCl; 10 mM $MgCl_2$; 0.3 mM $MnCl_2$; 20 Units of RNAse inhibitor; 10 μg of actinimycin D per mL; 0.5 mM ATP,GTP, and UTP; 10 μCi of [α-$P^{32}$] CTP; and 6 μl of the membrane fraction of a cell line expressing the viral replicon RNA in a total volume of 60 μl. The replication reaction is continued for a time sufficient to produce a desired amount of newly synthesized RNA.

In some embodiments, the replication conditions may include adding a 2'-O-methylated nucleotide such as, for example, 2'-O-methyl-5-methyluridine-5'-triphosphate to the replication mixture. The inclusion of a 2'-O-methylated nucleotide such as 2'-O-methyl-5-methyluridine-5' triphosphate may increase the efficiency of the replication complex, resulting in an increase in the amount of labeled product obtained in the absence of the 2'-O-methyl-5-methyluridine-5'-triphosphate. Without being held to a particular theory, it is believed that a 2'-O-methylated nucleotide, particularly 2'-O-methyl-5-methyluridine-5'-triphosphate increases the efficiency of the replicase complex when a radiolabeled nucleotide such as, for example, $P^{32}$-CTP is added to the reaction at low concentrations.

Suitable labeled nucleotide analogs include, for example, analogs which are capable of being recognized by specific antibodies (e.g., Br-UTP), analogs such as a biotin labeled nucleotide (e.g., biotin-CTP) which can be recognized via a high specificity binding reaction (i.e., biotin/avidin or biotin/streptavidin binding), and analogs which are directly detectable as a result of a physical property of the analog, such as radioactivity (e.g., a $P^{32}$-labeled nucleotide), fluorescence, luminescence etc., for example a fluorescein-nucleotide (e.g., fluorescein-UTP). In one embodiment, the labeled nucleotide analog is 5'-bromouridine 5'-triphosphate (Br-UTP). The RNA containing Br-UTP may be isolated by immuno-precipitation and/or detection with an anti-BrdU antibody. The anti-BrdU antibody may optionally be labeled with a tag suitable for direct detection of the antibody such as, for example, fluorescein, or other dyes such as those available from Molecular Probes. In other cases, the antibody may be detected via binding to a labeled secondary antibody such as, for example, a rabbit or mouse IgG labeled with alkaline phosphatase or horseradish peroxidase.

The labeled nucleotide analog is added to the replication mixture so that the labeled nucleotide analog is incorporated into the newly synthesized RNA (e.g., newly synthesized viral replicon RNA) in place of at least a portion of the corresponding unlabeled nucleotide. For example, Br-UTP may be used in place of at least a portion of the UTP. In certain cases, all of the corresponding nucleotide may be replaced with the labeled nucleotide analog. After replication, there are two populations of RNA (e.g., viral replicon RNA): an unlabeled RNA population (i.e., the RNA population present before replication) and a labeled RNA population (e.g., the newly synthesized RNA population). The newly synthesized RNA population, which contains the labeled nucleotide analog, can be distinguished from the RNA population which was present before the replication step, because the RNA population which was present before replication will not contain the labeled nucleotide analog. Because the newly synthesized RNA can be distinguished from the RNA present prior to replication, the amount of newly synthesized RNA (e.g., viral replicon RNA) can be detected and/or quantified by employing a means of RNA detection and/or quantitation. The means for RNA detection and quantitation may be the same or different.

After replication, the RNA in the replication mixture optionally may be purified using, for example, a commercially available RNA purification kit. The newly synthesized RNA is then detected using a means for detecting the RNA. Detection preferably comprises quantitative detection. The method for detecting the RNA is selected based on the labeled nucleotide analog employed. For example, in the case of an analog capable of being recognized by specific antibodies, a specific antibody may be employed to immuno-precipitate the labeled RNA. The immuno-precipitated RNA may be detected, for example, by directly detecting a fluorescent tag present on the antibody. Alternatively, the immuno-precipitated RNA may be detected with a labeled secondary antibody. In another alternative, the immuno-precipitated labeled RNA can be amplified and detected using real-time PCR.

For example, a newly synthesized RNA population containing Br-UTP as the labeled nucleotide analog may be immuno-precipitated using an anti-BrdU monoclonal antibody. The unlabeled, template RNA will not be precipitated, while the newly synthesized Br-UTP-labeled RNA will be specifically precipitated. The immuno-precipitated, labeled RNA may then be quantified using real time PCR. Thus, in the case of, for example, a Br-UTP labeled viral replicon RNA precipitated with anti-BrdU antibody, the method for detection comprises contacting the population of viral replicon RNAs with an anti-BrdU antibody, precipitating the viral replicon RNAs, and detecting and quantitating the labeled viral replicon RNAs using a suitable method such as, for example, real time PCR.

Real time PCR (polymerase chain reaction) is a quantitative reverse transcription-PCR reaction (RT-PCR). Early in RT-PCR, reagents are in excess, template and product are at low enough concentrations that product renaturation does not compete with primer binding, and amplification proceeds at a substantially constant, exponential rate. At some variable point during the reaction, the reaction rate ceases to be exponential, and enters a linear phase of amplification. Late in the amplification cycle, little product is made. Real time PCR allows the collection of data during the exponential phase of amplification, and thus allows for accurate quantitation of the amount of amplified product. Detection and quantitation of the double-stranded DNA produced in the PCR reaction is done using a fluorescent reporter, the signal of which increases in direct proportion to the amount of double-stranded DNA PCR product in a reaction. Taqman® probes labeled with fluorescent dye such as FAM (6-carboxy-fluorescein) may be used. Another suitable reporter is the double-strand DNA-specific dye SYBR® Green (Molecular Probes). SYBR® Green binds double-stranded DNA, and upon excitation emits light. Thus, as a PCR product accumulates, fluorescence increases. Other alternatives reporters include hybridization probes which use fluorescence energy transfer (FRET) for detection.

When the labeled nucleotide analog is a radioactive nucleotide such as $P^{32}$-CTP, the labeled RNAs may be detected by non-denaturing gel electrophoresis followed by autoradiography, direct radioactive detection such as Phosphorimaging, and the like.

In the case of a labeled nucleotide analog which can be recognized via a high specificity binding reaction, the labeled RNAs may be isolated by employing the high specificity binding reaction. For example, a biotin-labeled nucleotide can be recognized by avadin or streptavadin. Once the labeled RNAs have been isolated, the labeled RNAs can be amplified and detected using real-time PCR. In the case of a directly detectable nucleotide analog, the labeled nucleotide analog can be directly detected using fluorescence, luminescence, and the like.

Suitable controls for quantitation of the newly synthesized RNA population follow. Template RNAs isolated from cells untransfected with a DNA vector or viral RNA and subjected to replication, have no detectable amount of newly synthesized RNA. Template RNAs isolated from cells transfected with a template DNA vector or viral RNA, but replicated without the labeled nucleotide analog, have only background levels of newly synthesized RNA. Template RNAs from cells transfected with template DNA vector or viral RNA, replicated in the presence of a labeled nucleotide analog, which are not detected with the means for detection, show only background levels of newly synthesized RNA. Template RNAs from cells transfected with template DNA vector or viral RNA, replicated in the presence of labeled nucleotide analog and detected with the means for detection should, however, show a strong newly synthesized RNA signal in this assay.

The assay may be employed to quantitate a newly initiated RNA population. In the case of HCV, for example, most (e.g., about 90%) of the newly synthesized viral RNAs are the elongation products of previously initiated (i.e., initiated) template RNAs. In an initiated template RNA, a portion of the newly synthesized RNA is previously made using a minus strand template. Upon addition of the appropriate factors (e.g., buffers and nucleoside triphosphates), elongation of the initiated RNA can proceed to form the full-length RNA. Only a small fraction (e.g., less than about 10%) of the newly synthesized RNAs represent newly initiated products formed from uninitiated template RNAs (i.e., pre-initiation). Both the previously initiated and newly initiated RNAs will comprise the labeled nucleotide analog in the elongation region of the RNA. Only the newly initiated RNAs, however, will comprise the labeled nucleotide analog in the transcription initiation region. A method to select and quantitate newly initiated RNAs comprises employing RNA protection to the newly synthesized RNA population which may comprise a previously initiated RNA population as well as newly initiated RNAs.

In the RNAse protection assay, a nucleic acid probe is added to the newly synthesized viral replicon RNA population which may comprise previously initiated RNAs as well as newly initiated RNAs. The nucleic acid probe comprises a region complementary at least a portion of the transcription initiation region of the viral replicon RNAs (e.g., the newly synthesized RNA population). When the probe is hybridized to the population of newly synthesized viral replicon RNAs, a portion of the transcription initiation region becomes double-stranded, with the remainder of the RNA being single-stranded. The single-stranded RNA may then be removed, for example, by digestion with a single-strand specific ribonuclease specific for single-stranded RNA. Suitable single-strand specific ribonucleases include, for example, ribonuclease T1, ribonuclease A, nuclease S1, and combinations comprising one or more of the foregoing single-strand specific ribonucleases. After digestion, the remaining RNA will thus be a double-stranded RNA (i.e., protected) population in which the previously initiated RNAs will comprise no labeled nucleotide analog, and the newly initiated RNAs comprise the labeled nucleotide analog. The protected newly initiated RNAs can then be detected and/or quantified as described above.

Hybridization of the probe may be performed under conditions which are sufficient to allow specific hybridization of the nucleic acid probe to the viral replicase RNA. Specific hybridization can be performed under high stringency conditions or moderate stringency conditions, for example.

In a particularly preferred embodiment, the hybridization conditions for specific hybridization are high stringency.

The assay described herein may be employed to screen test compounds for inhibition of viral replicon RNA synthesis. Such compounds include replicase complex activity inhibitors as well as RNA synthesis initiation and elongation inhibitors. The method may be employed to distinguish initiation inhibitors from elongation inhibitors. If a viral replicon RNA synthesis inhibitor is added to a replication mixture, less viral replicon RNA should be synthesized, and the amount of labeled viral replicon RNA detected will be decreased (e.g., test RNA amount) relative to the amount of viral replicon RNA in a control sample (i.e., control RNA amount) with no added inhibitor. The amount of labeled viral replicon RNA detected will be decreased, for example, if the viral replicon RNA synthesis inhibitor is a viral replicon RNA elongation inhibitor. Viral replicon RNA elongation inhibitors will block synthesis of newly initiated viral replicon RNA elongation products and also previously initiated viral replicon RNA elongation products. If, however, the viral replicon RNA synthesis inhibitor is an initiation inhibitor, signal strength will be only modestly affected. Most (e.g., approximately 90%) of the newly synthesized viral RNAs of HCV are the elongation products of previously initiated viral replicon RNAs. Thus, only a small fraction (e.g., less than about 10%) of the newly synthesized replicon RNAs will be affected by an initiation inhibitor. FIG. 1 provides a schematic of the inhibition of HCV RNA synthesis by initiation and elongation inhibitors.

An RNAse protection assay, as described herein, can be added after formation of the newly synthesized RNA population to identify initiation inhibitors. In this assay, a nucleic acid probe which is complementary to at least a portion of the initiation region of the newly synthesized viral replicon is employed. The probe is hybridized to the viral replicon RNA such that the region of the viral replicon RNA complementary to the probe is double-stranded (i.e., replicated), and the remainder of the viral replicon RNA is single-stranded. Hybridization is preferably performed under stringent conditions. The single-stranded portion of the viral replicon RNA is then digested with a ribonuclease specific for single-stranded RNA such as, for example, ribonuclease A, ribonuclease T1, nuclease S1, or a combination comprising one or more of the foregoing ribonucleases. The remaining population of double-stranded replicon RNA will then contain two fractions: a fraction of previously initiated viral replicon RNAs which comprise no labeled nucleotide analog, and a fraction of viral replicon RNAs initiated after addition of the labeled nucleotide analog which comprise the labeled nucleotide analog. The protected viral replicon RNAs containing the labeled nucleotide analog can then be specifically detected and/or quantified as described above.

In the case of HCV, an exemplary probe is an RNA complimentary to nucleotides 15 to 433 of the HCV replicon RNA (SEQ ID NO:6), which hybridizes with the newly synthesized viral replicase RNA near the initiation codon. The RNA not hybridized to the probe is digested with a single-stranded ribonuclease, leaving only nucleotides 15 to 433 of the replicon RNA. The digested RNA will have two double-stranded RNA populations: a population of previously initiated replicon RNAs which do not contain the labeled nucleotide analog, and a population of newly initiated replicon RNAs which contain the labeled nucleotide analog. Thus, previously initiated HCV RNA elongation products will not be detected, while newly synthesized RNAs will be detected. In this assay including RNA protection, when an initiation inhibitor is added to the replication mixture, a reduced amount of labeled nucleotide analog is incorporated at the initiation site, and the signal measured by the means for detection will be decreased.

In positive strand RNA viruses, the replicase complex is a multi-protein complex which replicates viral replicon RNA from a viral replicon template RNA. Replicase complexes which include viral replicon template RNAs in addition to replication proteins can be isolated as a membrane bound fraction from cells expressing the viral replicon RNA. The isolated replicase complexes may include both previously initiated and uninitiated viral replicon template RNAs. Upon addition of nucleotide triphosphates and other components sufficient for RNA synthesis, elongation of previously initiated template RNAs proceeds to produce full-length viral replicase RNAs. It had not, however, been demonstrated that de novo initiation of uninitiated viral replicon template RNAs occurs in isolated replicase complexes. By using an inhibitor of initiation of viral replicon RNA synthesis initiation, it can be shown that de novo initiation of viral replicase RNA synthesis occurs in isolated replicase complexes. Because de novo initiation of RNA synthesis takes place in the isolated replicase complexes, the methods may be used to quantify newly initiated RNA and also to identify inhibitors of RNA synthesis initiation.

Thus, the described methods are suitable for detecting inhibitors of RNA synthesis of positive strand RNA viruses such as RNA initiation and elongation inhibitors.

Also provided herein is a kit for screening a test compound for inhibition of RNA synthesis of a positive strand RNA virus. The kit comprises an isolated replicase complex for the positive strand RNA virus, and isolated viral replicon template RNA for the positive strand RNA virus, instructions for use of the kit, and buffers and nucleoside triphosphates which are sufficient for synthesis of the viral replicon RNA. Instructions may include, for example, instructions for quantitating a newly synthesized RNA population, instructions for determining if a compound is an RNA synthesis inhibitor, and the like. The instructions may be written instructions, although electronic storage media (e.g., magnetic diskette or optical disk) containing instructions are also acceptable, relating to the use of components of the methods. The instructions included with the kit may include information as to reagents (e.g., whether included or not in the kit) necessary for practicing the methods, instructions on how to use the kit, and/or appropriate reaction conditions.

Suitable buffers include those described previously as suitable for performing replication with isolated replication complexes.

The kits may optionally further comprise, for example, a labeled nucleotide analog, a means for detecting and/or quantitating a labeled nucleotide analog, a primer, a single-strand specific ribonuclease, and instructions for performing an RNAse protection assay.

The component(s) of the kit may be packaged in a convenient, appropriate packaging. The components may be packaged separately, or in one or multiple combinations.

The invention is further illustrated by the following non-limiting examples.

EXAMPLES

Example 1

Growth And Maintenance of HCV Replicon Containing Cells

RNA molecules encoding the HCV replicon (i.e., viral replicon RNAs) are transfected into Huh-7 cells using electroporation.

The equipment and materials for cell maintenance include, but are not limited to, Huh-7 HCV replicon-containing cells, maintenance media (DMEM (Dulbecco's modified Eagle media) supplemented with 10% FBS (fetal bovine serum), L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, and non-essential amino acid, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-Nl 1, and enhancement solution.

Cells containing the HCV replicon support high levels of viral RNA replication when their density is suitable. Over-confluency may cause decreased viral RNA replication. Therefore, cells should be grown in log phase in the presence of 500 micrograms/ml of G418. Generally, cells should be passed twice a week at 1: 4-6 dilution. Cell maintenance is conducted as follows:

Cells containing the HCV replicon DNA vector are examined under a microscope to ensure that the cells are growing well. Cells are rinsed once with phosphate buffered saline (PBS) and 2 ml trypsin is added. The cell/trypsin mixture is incubated at 37° C. in a $CO_2$ incubator for 3-5 minutes. After incubation, 10 ml of complete media is added to stop the trypsinization reaction. Cells are blown gently, put into a 15 ml tube, and spun at 1200 rpm for 4 minutes. The trypsin/medium solution is removed and the pelleted cells are recovered.

Example 2

Quantitative Assay for Detection of Newly Synthesized HCV RNA in Cell-free System Membrane Fractions are purified from Huh-7 cells transfected with the HCV replicon RNA according to the procedure given by Hardy, et al. (*J. Virol.* (2003) 77:2029-2037). Briefly, the HCV replicon-containing cells are washed with 1×PBS, re-suspended in cold hypotonic buffer (10 mM Tri-HCl, pH 7.8, 10 mM NaCi), and put on ice for 20 minutes. The swelled cells are disrupted using a dounce homogenizer. The mix is centrifuged at 900 ×g for 5 minutes at 4° C. The supernatant is transferred to a fresh tube and centrifuged at 15000×g for 25 minutes at 4° C. The pellet, which contains the membrane fraction, is re-suspended in storage buffer (hypotonic buffer with 15% glycerol), and may be stored at −80° C.

In vitro RNA replication is performed according to the procedure of Lai (*J Virol.* (2003) 77:2295-2300) with some modifications. Test compound (1 μM to 100 μM in 0.5 μl DMSO) is pre-incubated the membrane fraction (isolated replicase complexes and isolated viral replicon template RNA) (10 μl) for 10 minutes at 30° C. before the replication mix is added. The replication mix (50 μl total volume) contains 50 mM HEPES (pH 7.5), 10 mM KCl, 10 mM $MgCl_2$ 50 U RNAsin, 10 μg/ml actinomycin D, 2.5 mM ATP, 0.5 mM each CTP, GTP, Br-UTP and the pre-incubated membrane fraction (i.e., the replicase complex and viral replicon template RNA). The replication mix is incubated at 30° C. for 2 hours, followed by purification using TRIZOL (Invitrogen, Carlsbad, Calif.) or RNA EASY (Qiagen, Valencia, Calif.) according to manufacturer's instructions. The RNA samples are then immuno-precipitated using anti-BrdU monoclonal antibody (Molecular Probes, Eugene, Oreg.) and protein A agarose (Invitrogen) in 200 μl to 400 μl of precipitation buffer containing 1×PBS, 0.05% NP 40, 0.1 μg/μl tRNA, 5 U/μl RNasin, and 0.3 M uridine.

When the newly synthesized segment near the initiation site is of interest, an RNA protection assay is used after Br-UTP labeling and RNA purification. The RNA probe for segment from 15 to 433 nt (SEQ ID NO: 6) is synthesized using an in vitro transcription kit (MAXIscript, Ambion). The DNA template for in vitro transcription was made by PCR using forward primer 5' GGGGGCGACACTCCACCATAGAT (15-37) (SEQ ID NO: 7) and reverse primer 5' ATTTAGGTGACACTATAGAAACCCAAGCGGCCGGAGAACCT (413-433, plus SP6 core sequence) (SEQ ID NO:8) on DNA vector for replicon HCV RNA or cDNA made from replicon HCV RNA by reverse transcription. The RNA is protected using an RNA protect assay kit (e.g. RPA III, Ambion, Austin, Tex.). Briefly, in the RNA protection assay, the newly synthesized replicon RNAs are hybridized to the RNA probe. The hybridized RNAs are then treated with a mixture of ribonuclease A and ribonuclease T1 to digest the single-stranded RNA. The remaining double-stranded RNA may then be precipitated prior to detecting.

The newly synthesized HCV RNA produced in the cell-free system is quantitatively detected using real time PCR. Table 1 shows the data for several control experiments. A Taqman® probe labeled with fluorescent dye FAM was used.

TABLE 1

| Sample | Copy number after PCR with no immuno-precipitation with anti-BrdUTP antibody | Copy number after PCR performed after immuno-precipitation with anti-BrdUTP antibody |
|---|---|---|
| Template RNA isolated from Huh-7 cells expressing HCV replicon with Br-UTP | $1.86 \times 10^7$ | $2.05 \times 10^5$ |
| Template RNA isolated from Huh-7 cells expressing HCV replicon with Br-UTP: No anti-Brd-UTP antibody | $1.85 \times 10^7$ | 2401 |
| Membranes isolated from Huh-7 cells with no HCV (no HCV template RNA) | 15 | 3 |
| Template RNA isolated from Huh-7 cells expressing HCV replicon: No Br-UTP in replication | $1.79 \times 10^7$ | 7270 |

As seen from Table 1, for template RNA isolated from Huh-7 cells expressing the HCV replicon with Br-UTP in the replication mixture, a high copy number of replicon RNA is observed both with and without precipitation with an anti-BrdUTP antibody. If no anti-BrdUTP antibody is used, the sample without precipitation has a high copy number of HCV replicon RNA, while the precipitated population has only a background amount. If the Huh-7 cells are not transfected with the HCV replicon (i.e., no template RNA), a background amount of replicon RNA is observed with or without precipitation with an anti-BrdU antibody. If there is no Br-UTP in the replication mixture with template RNA isolated from Huh-7 cells expressing the HCV replicon, the sample without precipitation has a high copy number of HCV replicon RNA, while the precipitated population has only a background amount. Thus, the control experiments give the expected results.

As shown in Table 2, the copy number of the HCV RNA measured by quantitative PCR is dependent upon the amount of template RNA added to the replication mixture. In Table 2, HCV is a replication mixture with template RNA isolated from Huh-7 cells expressing the HCV replicon. HVC (½) and HCV (⅛) are replication mixtures containing ½ and ⅛ of the amount of template RNA, respectively. Huh-7 (no HCV) is a no HCV template control as described above. No Br-UTP is a control in which template RNA isolated from Huh-7 cells expressing the HCV replicon, but no Br-UTP is added to the replication mixture.

TABLE 2

| Sample | Copy number after PCR with no immuno-precipitation with anti-BrdUTP antibody | Copy number after PCR performed after immuno-precipitation with anti-BrdUTP antibody |
|---|---|---|
| HCV | $2.19 \times 10^7$ | $7.34 \times 10^5$ |
| HCV (½) | $1 \times 10^7$ | $3.7 \times 10^5$ |
| HCV (⅛) | $3.1 \times 10^6$ | $1.51 \times 10^5$ |
| Huh-7 (No HCV) | 19 | 2030 |
| No Br-UTP | $2.17 \times 10^7$ | $4.6 \times 10^4$ |

As shown in Table 2, the copy number of HCV replicons measured in the assay, both with and without precipitation with an anti-BrdUTP antibody, is directly proportional to the amount of template replicon RNA added to the reaction mixture.

Table 3 shows the data for a known HCV RNA replication inhibitor that is tested using the disclosed assay at a concentration of 10 μM. The test compound is a published compound (Dhanak et al., *J. Biol. Chem.* (2002) 41):38322-7. The structure of the test compound is shown below.

TABLE 3

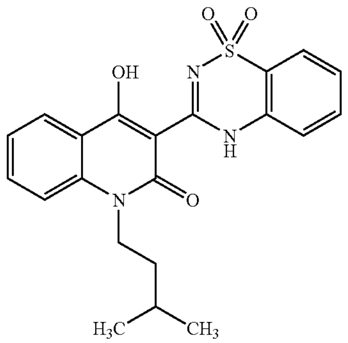

4

| Sample | Copy number after PCR with no RNAse protection assay | Copies as % of samples with no test compound | Copy number after PCR with RNAse protection assay | Copies as % of samples with no test compound |
|---|---|---|---|---|
| No test compound | 46942 | 100 | 137494 | 100 |
| Test compound | 31156 | 66 | 16970 | 12 |

In Table 3, although treatment with the test compound results in less than half reduction in total viral RNA synthesis with no RNAse protection, it causes close to a 10-fold reduction in the amount of newly initiated viral RNA synthesis after performing RNAse protection. Thus, the test compound inhibits HCV RNA synthesis at the initiation stage.

The results reported in this example validate this assay for compound screening and profiling. The assay has the advantage of quantitatively detecting newly synthesized HCV RNA, and permitting but also specific segment of our choice.

Example 3

Use of an RNA Initiation Inhibitor to Demonstrate de novo Initiation of Replication in Isolated Replication Complexes An RNA replication assay was used to determine if the replication complexes isolated from a membrane fraction were enzymatically active. The test compound (an initiation inhibitor) was employed to determine if the isolated replication complexes were capable of de novo initiation of newly synthesized RNA. Standard replication mixtures contained 50 mM HEPES (pH 7.3); 10 mM KCl; 10 mM $MgCl_2$; 0.3 mM $MnCl_2$; 20 Units of RNAse inhibitor; 10 μg of actinimycin D per mL; 0.5 mM ATP, GTP, and UTP; 10 μCi of [$\alpha$-$P^{32}$] CTP; and 6 μl of the membrane fraction in a total volume of 60 μl. The reaction mixtures were incubated at 30° C. for 2 hours. The RNA products were extracted with phenol-chloroform, ethanol precipitated, and separated on a non-denaturing 1% agarose gel. After electrophoresis, the gel was fixed with 10% glacial acetic acid then in ethanol and dried prior to autoradiography.

Figure 2:
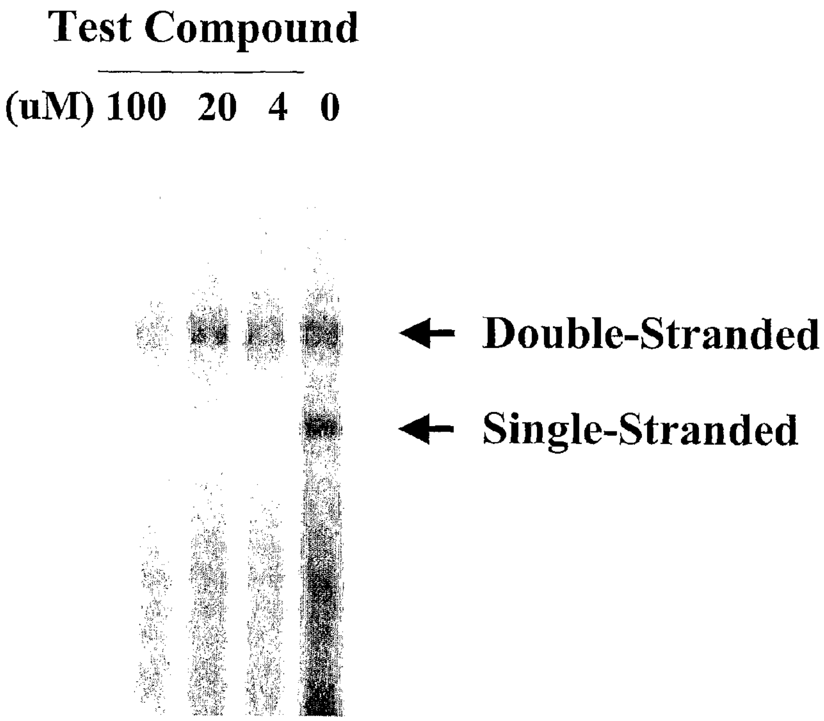
FIG. 2 shows an autoradiogram illustrating use of an RNA synthesis inhibitor to demonstrate de novo initiation of RNA synthesis in isolated replication complexes.

FIG. 2 shows an autoradiogram of the experimental results. Lane 4 is a control lane with no added inhibitor. Lanes 1-3 show the results with initiation inhibitor concentrations of 100, 20, and 4 μM, respectively. As clearly shown in the autoradiogram, addition of the initiation inhibitor reduces the amount of single-stranded RNA produced by the replication complex. In the assay, double-stranded RNA is produced largely from elongation of previously initiated RNAs, while single-stranded RNA is produced from newly initiated RNAs. The presence of a single-stranded RNA band in control lane 4 shows that newly initiated RNAs are formed during replication. When the test compound, a known RNA synthesis initiation inhibitor, is added during replication, the single-stranded RNA band disappears, while the double-stranded RNA band remains. Thus, by employing an RNA synthesis initiation inhibitor, it is confirmed that de novo RNA synthesis initiation occurs in isolated replicase complexes.

A method has been described to identify inhibitors of viral replicon RNA synthesis using detection and/or quantitation of a population of newly synthesized RNA. A decrease in the amount of newly synthesized RNA made in the presence of a test compound compared to a control with no test compound indicates that the test compound is a viral replicon RNA synthesis inhibitor. The method is particularly useful for identifying RNA elongation inhibitors. In addition, an RNAse protection assay may be employed on the newly synthesized RNA to identify RNA initiation inhibitors. It has been clearly demonstrated that isolated replication complexes are capable of de novo initiation in addition to elongation of previously initiated RNA. An advantage of the method is that initiation inhibitors can be distinguished from elongation inhibitors. Another advantage is that quanititation of the newly synthesized RNA population is employed to identify viral replicon RNA synthesis inhibitors. Another advantage is that a 2'-O-methylated nucleotide can be used to increase the yield of newly synthesized RNA produced during replication.

From the foregoing it will be appreciated that, although specific embodiments of the invention have been described herein for purposes of illustration, various modifications may be made without deviating from the spirit and scope of the invention.

The invention claimed is:

1. A method for quantitating newly initiated RNA of a positive strand RNA virus comprising:

contacting an isolated replicase complex for the positive strand RNA virus, an isolated viral replicon template RNA for the positive strand RNA virus, nucleotides, and a labeled nucleotide analog, and 2'-O-methyl-5-methyluridine-5'- triphosphate under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of a transcription initiation region of the newly synthesized RNA population;

digesting unhybridized, single-stranded RNA with a single-strand specific ribonuclease to form a protected RNA population comprising the labeled nucleotide analog;

detecting the protected RNA population comprising the labeled nucleotide analog; and quantitating the protected RNA population comprising the labeled nucleotide analog.

2. The method of claim 1, further comprising providing the isolated replicase complex and the isolated viral replicon template RNA by:

transfecting a human hepatoma cell line with a viral replicon RNA or a DNA template for a viral replicon to provide a transfected cell line, incubating the transfected cell line under conditions suitable for production of viral replicase complexes, and isolating the replicase complexes comprising the viral replicon template RNA from the cell membrane fraction of the transfected cells.

3. The method of claim 2, wherein the DNA template for the viral replicon is SEQ ID NO: 1, SEQ ID NO: 2, SEQ ID NO:3, SEQ ID NO: 4, or SEQ ID NO: 5.

4. The method of claim 1, wherein the labeled nucleotide analog is an analog capable of being recognized by a specific antibody, an analog which can be recognized via a specific binding reaction, or an analog directly detectable as a result of a physical property of the analog.

5. The method of claim 1, wherein the positive strand RNA virus is Hepatitis C Virus.

6. A method for determining whether a test compound is an RNA synthesis initiation inhibitor of a positive strand RNA virus comprising:

contacting an isolated replicase complex for the positive strand RNA virus, an isolated viral replicon template RNA for the positive strand RNA virus, nucleotides, a labeled nucleotide analog, 2'-O-methyl-5-methyluridine-5'- triphosphate, and the test compound, under conditions sufficient for in vitro RNA synthesis, to form a newly synthesized RNA population comprising the labeled nucleotide analog;

hybridizing a probe and the newly synthesized RNA population comprising the labeled nucleotide analog, under stringent hybridization conditions, wherein the probe is complementary to at least a portion of an initiation region of the newly synthesized RNA population;

digesting unhybridized, single-stranded RNA with a single-strand specific ribonuclease to form a protected RNA population comprising the labeled nucleotide analog;

detecting the protected RNA population comprising the labeled nucleotide analog;

quantitating the protected RNA population comprising the labeled nucleotide analog to provide a test RNA amount; and comparing the test RNA amount with a control RNA amount of protected RNA comprising the labeled nucleotide analog but produced in the absence of the test compound, wherein a decrease in the test RNA amount compared to the control RNA amount indicates that the test compound inhibits RNA synthesis initiation of the positive strand RNA virus.

* * * * *